(12) United States Patent
Mueller-Hermelink et al.

(10) Patent No.: US 7,741,444 B2
(45) Date of Patent: Jun. 22, 2010

(54) NEOPLASM SPECIFIC ANTIBODIES AND USES THEREOF

(75) Inventors: Hans-Konrad Mueller-Hermelink, Würzburg (DE); Heinz Peter Vollmers, Würzburg (DE)

(73) Assignee: Patrys Limited, Melbourne Victoria (AU)

( * ) Notice: Subject to any disclaimer, the term of this patent is extended or adjusted under 35 U.S.C. 154(b) by 0 days.

(21) Appl. No.: 11/838,603

(22) Filed: Aug. 14, 2007

(65) Prior Publication Data

US 2008/0020457 A1 Jan. 24, 2008

Related U.S. Application Data

(62) Division of application No. 10/520,224, filed as application No. PCT/IB03/03487 on Jul. 2, 2003.

(30) Foreign Application Priority Data

| Jul. 4, 2002 | (DE) | ................ 102 29 906 |
| Jul. 4, 2002 | (DE) | ................ 102 29 907 |
| Jul. 6, 2002 | (DE) | ................ 102 30 516 |

(51) Int. Cl.
C07K 16/00 (2006.01)
C07K 16/30 (2006.01)
C12P 21/06 (2006.01)

(52) U.S. Cl. ............ 530/387.1; 530/387.3; 530/387.7; 530/388.1; 530/388.15; 530/388.8; 530/809

(58) Field of Classification Search ................ None
See application file for complete search history.

(56) References Cited

U.S. PATENT DOCUMENTS

| 5,001,225 | A | 3/1991 | Taylor ............ 530/388.6 |
| 5,610,280 | A | 3/1997 | Brandt et al. ........ 530/387.5 |
| 5,639,863 | A | 6/1997 | Dan ............... 530/388.8 |
| 5,763,224 | A | 6/1998 | Caras et al. ........ 435/69.6 |
| 6,677,442 | B1 | 1/2004 | Wang et al. ........ 536/23.2 |
| 6,995,240 | B1 | 2/2006 | Panayi et al. ......... 530/350 |
| 7,049,132 | B1 | 5/2006 | Lee .............. 435/320.1 |
| 2003/0105000 | A1* | 6/2003 | Pero et al. ............ 514/12 |
| 2004/0180002 | A1 | 9/2004 | Young et al. ......... 424/1.49 |
| 2004/0197328 | A1* | 10/2004 | Young et al. ........ 424/141.1 |
| 2004/0258693 | A1* | 12/2004 | Young et al. ........ 424/155.1 |
| 2005/0123571 | A1 | 6/2005 | Rossini et al. ......... 424/277.1 |

FOREIGN PATENT DOCUMENTS

| DE | 41 07 154 A1 | 4/1992 |
| DE | 692 12 671 T2 | 3/1997 |
| DE | 692 29 110 T2 | 11/1999 |
| DE | 695 27 975 T2 | 3/2003 |
| EP | 0 502 812 A1 | 8/1996 |
| EP | 0 502 812 B1 | 8/1996 |
| EP | 1 106 183 A2 | 6/2001 |
| EP | 1 106 183 A3 | 6/2001 |
| EP | 1 141 019 B1 | 4/2004 |
| WO | 92/16624 A1 | 10/1992 |
| WO | 96/16990 A1 | 6/1996 |
| WO | 97/02479 | 1/1997 |
| WO | 97/13844 A1 | 4/1997 |
| WO | 99/28461 | 6/1999 |
| WO | 99/53051 | 10/1999 |
| WO | 99/65935 A2 | 12/1999 |
| WO | 00/37489 A2 | 6/2000 |
| WO | 00/37489 A3 | 6/2000 |
| WO | 01/62932 A1 | 8/2001 |
| WO | 01/83560 A1 | 11/2001 |
| WO | WO/2003/048321 A2 * | 12/2001 |
| WO | 02/12502 A2 | 2/2002 |
| WO | 02/084277 A1 | 10/2002 |
| WO | 03/011907 A3 | 2/2003 |
| WO | 03/076472 A2 | 9/2003 |
| WO | 03/076472 A3 | 9/2003 |
| WO | 2004/005351 A2 | 1/2004 |
| WO | 2004/020999 A1 | 3/2004 |
| WO | 2004/081027 A2 | 9/2004 |
| WO | 2004/081027 A3 | 9/2004 |
| WO | 2005/001052 A2 | 1/2005 |
| WO | 2005/045428 A2 | 5/2005 |
| WO | 2005/047332 A1 | 5/2005 |
| WO | 2005/065418 A2 | 7/2005 |
| WO | 2005/092922 A2 | 10/2005 |
| WO | 2005/092922 A3 | 10/2005 |
| WO | 2005/094159 A2 | 10/2005 |

OTHER PUBLICATIONS

Overholser et al. (Cancer 2000 89 (1): 74-82).*
Goldstein et al. (Clin. Cancer Research 1995 1: 1311-1318)*
Berger, C.L., et al., A Lymphocyte Cell Surface Heat Shock Protein Homologous to the Endoplasmic Reticulum Chaperone, Immunoglobulin Heavy Chain Binding Protein BIP, Int. J. Cancer, 71:1077-1085 (1997).
Bjorge et al., Complement-Regulatory Proteins in Ovarian Malignancies, Int. J. Cancer, 70:14-25 (1997).
Brandlein et al., "Natural IgM Antibodies and Immunosurveillance Mechanisms Against Epithelial Cancer Cells in Humans," Cancer Research, 63: 7995-8005, Nov. 15, 2003.
Brändlein et al., Characterization of Five New Fully Human Monoclonal IgM Antibodies Isolated from Carcinoma Patients, Proceedings of the Annual Meeting of the American Association for Cancer Research 43:970, Mar. 2002 (Abstract).
Brändlein et al., Human Monoclonal IgM Antibodies with Apoptotic Activity isolated from Cancer Patients, Human Antibodies 11:107-119, 2002.
Brändlein, S., et al., CFR-1 Receptor as Target for Tumor-specific Apoptosis Induced by the Natural Human Monoclonal Antibody PAM-1, Oncology Reports, 11:777-784 (2004).
Brändlein, S., et al., Cysteine-rich Fibroblast Growth Factor Receptor 1, a New Marker for Precancerous Epithelial Lesions Defined by the Human Monoclonal Antibody PAM-1, Cancer Research, 63:2052-2061 (2003).

(Continued)

*Primary Examiner*—Peter J Reddig
(74) *Attorney, Agent, or Firm*—Pillsbury Winthrop Shaw Pittman LLP

(57) ABSTRACT

The present invention features polypeptides, such as antibodies, and their use in the treatment and diagnosis of neoplasms.

19 Claims, 17 Drawing Sheets

OTHER PUBLICATIONS

Brändlein, S., et al., PAM-1, a Natural Human IgM Antibody as New Tool for Detection of Breast and Prostate Precursors, Human Antibodies, 13:97-104 (2004).

Chen, G., et al., Protein Profiles Associated With Survival in Lung Adenocarcinoma, www.pnas.org/cgi/doi/10.1073/pnas.2233850100 pp. 1-6 (2003).

Database entry AAB02178 dated Jun. 11, 1996.

Faller et al., HAB-1, a New Heteromyeloma for Continuous Production of Human Monoclonal Antibodies, Br. J. Cancer 62:595-598 (1990).

Gibbs et al., The function of the Human Homolog of S. Cerevisiae REV1 is required for mutagenesis induced by UV light, PNAS 97:8, 4186-4191, Apr. 11, 2000.

Gonatas et al., MG-160, A Membrane Sialoglycoprotein of the Medial Cisternae of the Rat Golgi Apparatus, Binds Basic Fibroblast Growth Factor and Exhibits a High level of Sequence Identity to a Chicken Fibroblast Growth Factor Receptor, J. Cell Science 108:457-467, 1995.

Grossman, H.B., Natural Antibody to a Human Bladder Carcinoma Cell Line, Cancer Immunol. Immunother. 13:89-92 (1982).

Hensel et al., A New Variant of Cystein-Rich FGF Receptor (CFR-1) Specifically Expressed on Tumor Cells, Proceedings of the American Association for Cancer Research 41:698 (abstract 4438), Mar. 2000.

Hensel et al., A Novel Proliferation-associated Variant of CFR-1 Defined by a Human Monoclonal Antibody, Laboratory Investigation 81:1097-1108, 2001.

Hensel et al., Characterization of Glycosylphosphatidylinositol-linked Molecule CD55/Decay-accelerating Factor as the Receptor for Antibody SC-1-induced Apoptosis, Cancer Research 59:5299-5306, 1999.

Hensel et al., Mitogenic Autoantibodies in Helicobacter pylori-Associated Stomach Cancerogenesis, International Journal of Cancer 81:229-235, 1999.

Hensel, F., et al., "Regulation of the new coexpressed CD55 (decay-accelerating factor) receptor on stomach carcinoma cells involved in antibody SC-1-induced apoptosis", Laboratory Investigation, 81(11):1553-1563 (2001).

Huang et al., Sulindac Sulfide-induced Apoptosis Involves Death Receptor 5 and the Caspase 8-dependent Pathway in Human Colon and Prostate Cancer Cells, Cancer Research 61:6918-6924 (2001).

Jamora, C., et al., Inhibition of Tumor Progression by Suppression of Stress Protein GRP78/BiP Induction in Fibrosarcoma B/C1OME, Proc. Natl. Acad. Sci. USA, 93:7690-7694 (1996).

Jansson, et al., The Human Repertoire of Antibody Specificities Against Thomsen-Friedenreich and TN-carcinoma-associated antigens as defined by Monoclonal Antibodies, Cancer Immunology 34:294-298, 1992.

Kamitani, H., et al., Expression of 15-Lipoxygenase by Human Colerectal Carcinoma Caco-2 Cells During Apoptosis and Cell Differentiation, The Journal of Biological Chemistry, 273(34):21569-21577 (1998).

Lee, A.S., Mammalian Stress Response: Induction of the Glucose-Regulated Protein Family, Current Opinion in Cell Biology, 4:267-273 (1992).

Mammalian Gene Collection (MGC) Program Team, "Generation and Initial Analysis of more than 15,000 Full-Length Human and Mouse cDNA Sequences" PNAS USA 99:16,899-16,903 (2002).

Mintz, P.J., et al., Fingerprinting the Circulating Repertoire of Antibodies from Cancer Patients, Nature Biotechnology, 21:57-63 (2003).

Mourelatos et al., Cloning and Sequence Analysis of the Human MG160, a Fibroblast Growth Factor and E-Selectin Binding Membrane Sialoglycoprotein of the Golgi Apparatus, DNA Cell Biol. 12:1121-1128 (1996).

Pfaff, M., et al., Human Monoclonal Antibody Against a Tissue Polypeptide Antigen-related Protein from a Patient with a Signet-Ring Cell Carcinoma of the Stomach, Cancer Research, 50:5192-5198 (1990).

Sato, K., et al., Immunotherapy Using Heat-Shock Protein Preparations of Leukemia Cells After Syngenic Bone Marrow Transplantation in Mice, Blood, 98(6):1852-1857 (2001).

Sugawara, S., et al., Suppression of Stress Protein GRP78 Induction in Tumor B/C1OME Eliminates Resistance to Cell Mediated Cytotoxicity, Cancer Research, 53:6001-6005 (1993).

Timmermann W., et al., Immuntherapie: ein Antikörper gegen Magenkrebs Blick 1/1999, Artikel 6, internet page http://www.uni-wuerzburg.de/blick1999-1/991do6-t.html.

Vollmers et al., "Apoptosis of Stomach Carcinoma Cells Induced by a Human Monoclonal Antibody," Cancer 76:550-558 (1995).

Vollmers et al., "Human Monoclonal Antibodies from Stomach Carcinoma Patients React with Helicobacter pylori and Stimulate Stomach Cells in vitro," Cancer 74:1525-1532, 1994.

Vollmers et al., "SC-1, a Functional Human Monoclonal Antibody against Autologous Stomach Carcinoma Cells," Cancer Res. 49:2471-2476, 1989.

Vollmers et al., Adjuvant Therapy for Gastric Adenocarcinoma with the Apoptosis-Inducing Human Monoclonal Antibody SC-1: First Clinical and Histopathological Results, Oncology Reports 5:549-552 (1998).

Vollmers, H.P., et al., Monoclonal Antibodies NORM-1 and NORM-2 Induce More Normal Behavior of Tumor Cells In Vitro and Reduce Tumor Growth In Vivo, Cell, 40:547-557 (1985).

Vollmers, P., et al., Tumor-Specific Apoptosis Induced by the Human Monoclonal Antibody SC-1: A New Therapeutical Approach for Stomach Cancer, Oncology Reports, 5:35-40 (1998).

Wixler et al., "Identification of Novel Interaction Partners for the conserved membrane proximal region of alpha-integrin cytoplasmic domains," FEBS Letters vol. 445, Feb. 26, 1999.

Rudikoff, et al., Single Amino Acid Substitution Altering Antigen-Binding Specificity, Proc. Natl. Acad. Sci. USA, 79:1979-1983 (1982).

Gussow, et al., [5] Humanization of Monoclonal Antibodies, Methods in Enzymology 203:99-121 (1991).

MacCallum, et al., Antibody-Antigen Interactions: Contact Analysis and Binding Site Topography, J. Mol. Biol., 262:732-745 (1996).

Casset, et al., A Peptide Mimetic of an Anti-CD4 Monoclonal Antibody by Rational Design, BBRC, 307:198-205 (2003).

Wu, et al., Humanization of a Murine Monoclonal Antibody by Simultaneous Optimization of Framework and CDR Residues, J. Mol. Biol. 294:151-162 (1999).

Straub, et al., Cassette Mutagenesis of a Potential Substrate Recognition Region of Cytochrome P450 2C2, J. Biol. Chem., 268(29) 21997-20003 (1993).

Kouklis, et al., In Vitro Assembly Properties of Vimentin Mutagenized at the β-Site Tail Motif, J. Cell Science, 106(pt 3):919-28 (1993).

Roitt, et al., Immunology, Third Edition (Mosby, London England) p. 1.7 (1993).

Taber's Cyclopedic Medical Dictionary, F.A. Davis Company, Philadelphia, p. 274 (1985).

Kaiser, First Pass at Cancer Genome Reveals Complex Landscape, Science, 313:1370 (2006).

Krontiris and Capizzi, Internal Medicine, $4^{th}$ Edition, Editor-in-chief Jay Stein, Elsevier Science, 1994 Chapters 71-72, pp. 699-729.

Carter, S.K., et al., Chemotherapy of Cancer; Second Edition; John Wiley & Sons, New York, 1981, appendix C.

Freshney, Culture of Animal Cells, A Manual of Basic Technique, Alan R. Liss, Inc., 1983, New York, p. 4.

Dermer, Another Anniversary for the War on Cancer, Biotechnology, 12:320 (1994).

Drexler, et al., Recent Results on the Biology of Hodgkin and Reed-Sternberg Cells. II. Continuous Cell Lines, Leukemia and Lymphoma, 9:1-25 (1993).

Zellner, et al., Disparity in Expression of Protein Kinase C α in Human Glioma versus Glioma-derived Primary Cell Lines: Therapeutic Implications, Clinical Cancer Research, 4:1797-1802 (1998).

Zips, et al., New Anticancer Agents: In Vitro and In Vivo Evaluation, In Vivo, 19:1-8 (2005).

Gura, Systems for Identifying New Drugs Are Often Faulty, Science, 278:1041-042 (1997).

Janeway, et al., Immunobiology, 5:100-101 (2001).

Curti, Physical Barriers to Drug Delivery in Tumors, Crit. Rev. in Oncology/Hematology, 14:29-39 (1993).

Sambrook, et al., Molecular Cloning, 2nd Edition, Cold Spring Harbor Press, p. 18.47 (1989).

Colman, Effects of Amino Acid Sequence Changes on Antibody-Antigen Interactions, Research in Immunology, 145(1):33-36 (1994).

Burgess, et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Bio., 111:2129-2138 (1990).

Bowie, et al., Deciphering the Message in Protein Sequences: Tolerance to Amino Acid Substitutions, Science, 247:1306-1310 (1990).

* cited by examiner

A

B

A

B

PM-1 Light chain variable region sequence

```
tcc tat gtg ctg act cag cca ccc tcg gtg tca gtg tcc cca gga caa acg gcc agg atc        60
Ser Tyr Val Leu Thr Gln Pro Pro Ser Val Ser Val Ser Pro Gly Gln Thr Ala Arg Ile
 1               5                  10                  15                  20
                                  CDR1
acc tgc tct gga gat gca ttg cca aaa aaa tat cct tat tgg tac cag cag aag tca ggc       120
Thr Cys Ser Gly Asp Ala Leu Pro Lys Lys Tyr Pro Tyr Trp Tyr Gln Gln Lys Ser Gly
                 25                  30                  35                  40
                            CDR2
cag gcc cct gtg ctg gtc atc tat gag gac agc aaa cga ccc tcc ggg atc cct gag aga       180
Gln Ala Pro Val Leu Val Ile Tyr Glu Asp Ser Lys Arg Pro Ser Gly Ile Pro Glu Arg
                 45                  50                  55                  60 ttc tct ggc tcc agc tca ggg aca atg gcc acc ttg act atc agt ggg gcc cag gtg gag       240
Phe Ser Gly Ser Ser Ser Gly Thr Met Ala Thr Leu Thr Ile Ser Gly Ala Gln Val Glu
                 65                  70                  75                  80
                                      CDR3
gat gaa gct gac tac tac tgt tac tca aca gac agc agt ggt aat atg tct tcg gaa ctg       300
Asp Glu Ala Asp Tyr Tyr Cys Tyr Ser Thr Asp Ser Ser Gly Asn Met Ser Ser Glu Leu
                 85                  90                  95                 100 gga cca agc tca ccg tcc                                                               318
Gly Pro Ser Ser Pro Ser
                105
```

FIG. 12

PM-1 Heavy chain variable region sequence

```
                                                   CDR1
ggg tcc ctg aga ctc tcc tgt gca gcc tct gga ttc acc ttt agc agc tat gcc atg agc    60
Gly Ser Leu Arg Leu Ser Cys Ala Ala Ser Gly Phe Thr Phe Ser Ser Tyr Ala Met Ser
1               5                   10                  15                  20
                                                                       CDR2
tgg gtc cgc cag gct cca ggg aag ggg ctg gag tgg gtc tca gct att agt ggt agt ggt    120
Trp Val Arg Gln Ala Pro Gly Lys Gly Leu Glu Trp Val Ser Ala Ile Ser Gly Ser Gly
                    25                  30                  35                  40 ggt agc aca tac tac gca gac tcc gtg aag ggc cgg ttc acc atc tcc aga gac aat tcc    180
Gly Ser Thr Tyr Tyr Ala Asp Ser Val Lys Gly Arg Phe Thr Ile Ser Arg Asp Asn Ser
                45                  50                  55                  60 aag aac acg ctg tat ctg caa atg aac agc ctg aga gcc gag gac acg gcc gta tat tac    240
Lys Asn Thr Leu Tyr Leu Gln Met Asn Ser Leu Arg Ala Glu Asp Thr Ala Val Tyr Tyr
                65                  70                  75                  80
            CDR3
tgt gcg aaa gat tca ttt cgt gaa gga ccc tgg ggc cag gga acc ctg gtc acc            294
Cys Ala Lys Asp Ser Phe Arg Glu Gly Pro Trp Gly Gln Gly Thr Leu Val Thr
                85                  90                  95
```

FIG. 13

PM-2 Light chain variable region sequence

```
cag tct gcc ctg act cag cct gct tcc ctc tct gca tct cct gga gca tca gcc agt ctc    60
Gln Ser Ala Leu Thr Gln Pro Ala Ser Leu Ser Ala Ser Pro Gly Ala Ser Ala Ser Leu
 1               5                  10                  15                  20
                                          CDR1
acc tgc acc ttg cgc agt ggc atc aat gtt ggt acc tac agg ata tac tgg tac cag cag   120
Thr Cys Thr Leu Arg Ser Gly Ile Asn Val Gly Thr Tyr Arg Ile Tyr Trp Tyr Gln Gln
                25                  30                  35                  40
                                                      CDR2
aag cca ggg agt cct ccc cag tat ctc ctg agg tac aaa tca gac tca gat aag cag aag   180
Lys Pro Gly Ser Pro Pro Gln Tyr Leu Leu Arg Tyr Lys Ser Asp Ser Asp Lys Gln Lys
                45                  50                  55                  60 ggc tct gga gtc ccc agc cgc ttc tct gga tcc aaa gat gct tcg gcc aat gca ggg att   240
Gly Ser Gly Val Pro Ser Arg Phe Ser Gly Ser Lys Asp Ala Ser Ala Asn Ala Gly Ile
                65                  70                  75                  80
                                                                  CDR3
tta ctc atc tct ggg ctc cag tct gag gat gag gct gac tat tac tgt atg att tgg cac   300
Leu Leu Ile Ser Gly Leu Gln Ser Glu Asp Glu Ala Asp Tyr Tyr Cys Met Ile Trp His
                85                  90                  95                 100 agc agc gct tgg gtg ttc ggc gga ggg acc aag ctg acc gtc cta ggt                   348
Ser Ser Ala Trp Val Phe Gly Gly Gly Thr Lys Leu Thr Val Leu Gly
               105                 110                 115
```

FIG. 14

PM-2 Heavy chain variable region sequence

```
                                                            CDR1
ggg tcc ctg aga ctc tcc tgt gca gcc tct gga ttc acc ttt agc agc tat gcc atg agc        60
Gly Ser Leu Arg Leu Ser Cys Ala Ala Ser Gly Phe Thr Phe Ser Ser Tyr Ala Met Ser
 1               5                  10                  15                  20
                                                                    CDR2
tgg gtc cgc cag gct cca ggg aag ggg ctg gag tgg gtc tca gct att agt ggt agt ggt       120
Trp Val Arg Gln Ala Pro Gly Lys Gly Leu Glu Trp Val Ser Ala Ile Ser Gly Ser Gly
                25                  30                  35                  40 ggt agt aca tac tac gca gac tcc gtg aag ggc cgg ttc acc atc tcc aga gac aat tcc       180
Gly Ser Thr Tyr Tyr Ala Asp Ser Val Lys Gly Arg Phe Thr Ile Ser Arg Asp Asn Ser
                45                  50                  55                  60 aag aac acg ctg tat ctg caa atg aac agc ctg aga gcc gag gac acg gcc gta tat tac       240
Lys Asn Thr Leu Tyr Leu Gln Met Asn Ser Leu Arg Ala Glu Asp Thr Ala Val Tyr Tyr
                65                  70                  75                  80
                                        CDR3
tgt gcg aaa ggt ggg gcc gaa ggc tgg tac gag tac tac tac tac ggt atg gac gtc           300
Cys Ala Lys Gly Gly Ala Glu Gly Trp Tyr Glu Tyr Tyr Tyr Tyr Gly Met Asp Val
                85                  90                  95                 100 tgg ggc caa ggg acc ctg gtc                                                           321
Trp Gly Gln Gly Thr Leu Val
               105
```

FIG. 15

CM-2 Light chain variable region sequence

```
cag tct gcc ctg act cag cct gcc tcc gtg tct ggg tct cct gga cag tcg atc acc atc      60
Gln Ser Ala Leu Thr Gln Pro Ala Ser Val Ser Gly Ser Pro Gly Gln Ser Ile Thr Ile
  1           5                  10                  15                  20
                                    CDR1
tcc tgc act gga acc agc agt gac gtt ggt ggt tat aac tat gtc tcc tgg tac caa cag     120
Ser Cys Thr Gly Thr Ser Ser Asp Val Gly Gly Tyr Asn Tyr Val Ser Trp Tyr Gln Gln
                 25                  30                  35                  40
                                                CDR2
cac cca ggc aaa gcc ccc aaa ctc atg att tat gat gtc agt aat cgg ccc tca ggg gtt     180
His Pro Gly Lys Ala Pro Lys Leu Met Ile Tyr Asp Val Ser Asn Arg Pro Ser Gly Val
                 45                  50                  55                  60 tct aat cgc ttc tct ggc tcc aag tct ggc aac acg gcc tcc ctg acc atc tct gga ctc     240
Ser Asn Arg Phe Ser Gly Ser Lys Ser Gly Asn Thr Ala Ser Leu Thr Ile Ser Gly Leu
                 65                  70                  75                  80
                                                        CDR3
cag gct gag gac gag gct gat tac tac tgc agc tca aaa aga agc agc aac act cta gta     300
Gln Ala Glu Asp Glu Ala Asp Tyr Tyr Cys Ser Ser Lys Arg Ser Ser Asn Thr Leu Val
                 85                  90                  95                 100 ttc ggc gga ggg acc aag ctg acc gtc cta                                             330
Phe Gly Gly Gly Thr Lys Leu Thr Val Leu
                105                 110
```

FIG. 16

CM-2 Heavy chain variable region sequence

```
                                                              CDR1
aaa aag ccc ggg gag tct ctg agg atc tcc tgt aag ggc tct gga tac agt ttt acc acc    60
Lys Lys Pro Gly Glu Ser Leu Arg Ile Ser Cys Lys Gly Ser Gly Tyr Ser Phe Thr Thr
 1           5                  10                  15                  20 tac tgg atc ggc tgg gtg cgc cag atg ccc ggg aaa ggc ctg gag tgg atg ggg atc atc   120
Tyr Trp Ile Gly Trp Val Arg Gln Met Pro Gly Lys Gly Leu Glu Trp Met Gly Ile Ile
             25                  30                  35                  40
        CDR2
tat cct ggt gac tct gat acc aga tac agc ccg tcc ttc caa ggc cag gtc acc atc tca   180
Tyr Pro Gly Asp Ser Asp Thr Arg Tyr Ser Pro Ser Phe Gln Gly Gln Val Thr Ile Ser
                     45                  50                  55                  60 gcc gac acg tcc atc agt acc gcc tac ctg cag tgg agc agc ctg aag gcc tcg gac acc   240
Ala Asp Thr Ser Ile Ser Thr Ala Tyr Leu Gln Trp Ser Ser Leu Lys Ala Ser Asp Thr
                         65                  70                  75                  80
                                                CDR3
gcc ata tat tac tgt gcg agg gag gtc tat act ggc cga aac tac tac tac ggt ctg       300
Ala Ile Tyr Tyr Cys Ala Arg Glu Val Tyr Thr Gly Arg Asn Tyr Tyr Tyr Gly Leu
                 85                  90                  95                 100 gac gtc tgg ggc caa gga acc ctg gtc                                               327
Asp Val Trp Gly Gln Gly Thr Leu Val
                105
```

FIG. 17

SEQUENCE LISTING

```
<160> NUMBER OF SEQ ID NOS: 12

<210> SEQ ID NO 1
<211> LENGTH: 106
<212> TYPE: PRT
<213> ORGANISM: Homo sapiens

<400> SEQUENCE: 1

Ser Tyr Val Leu Thr Gln Pro Pro Ser Val Ser Val Ser Pro Gly Gln
 1               5                   10                  15
```

```
        Thr Ala Arg Ile Thr Cys Ser Gly Asp Ala Leu Pro Lys Lys Tyr Pro
                    20                  25                  30

Tyr Trp Tyr Gln Gln Lys Ser Gly Gln Ala Pro Val Leu Val Ile Tyr
                35                  40                  45

Glu Asp Ser Lys Arg Pro Ser Gly Ile Pro Glu Arg Phe Ser Gly Ser
                    50                  55                  60

Ser Ser Gly Thr Met Ala Thr Leu Thr Ile Ser Gly Ala Gln Val Glu
        65                  70                  75                  80

Asp Glu Ala Asp Tyr Tyr Cys Tyr Ser Thr Asp Ser Ser Gly Asn Met
                        85                  90                  95

Ser Ser Glu Leu Gly Pro Ser Ser Pro Ser
                    100                 105

<210> SEQ ID NO 2
<211> LENGTH: 318
<212> TYPE: DNA
<213> ORGANISM: Homo sapiens
<220> FEATURE:
<221> NAME/KEY: CDS
<222> LOCATION: (1)...(318)

<400> SEQUENCE: 2 tcc tat gtg ctg act cag cca ccc tcg gtg tca gtg tcc cca gga caa         48
Ser Tyr Val Leu Thr Gln Pro Pro Ser Val Ser Val Ser Pro Gly Gln
 1               5                   10                  15 acg gcc agg atc acc tgc tct gga gat gca ttg cca aaa aaa tat cct         96
Thr Ala Arg Ile Thr Cys Ser Gly Asp Ala Leu Pro Lys Lys Tyr Pro
            20                  25                  30 tat tgg tac cag cag aag tca ggc cag gcc cct gtg ctg gtc atc tat        144
Tyr Trp Tyr Gln Gln Lys Ser Gly Gln Ala Pro Val Leu Val Ile Tyr
        35                  40                  45 gag gac agc aaa cga ccc tcc ggg atc cct gag aga ttc tct ggc tcc        192
Glu Asp Ser Lys Arg Pro Ser Gly Ile Pro Glu Arg Phe Ser Gly Ser
            50                  55                  60 agc tca ggg aca atg gcc acc ttg act atc agt ggg gcc cag gtg gag        240
Ser Ser Gly Thr Met Ala Thr Leu Thr Ile Ser Gly Ala Gln Val Glu
65                  70                  75                  80 gat gaa gct gac tac tac tgt tac tca aca gac agc agt ggt aat atg        288
Asp Glu Ala Asp Tyr Tyr Cys Tyr Ser Thr Asp Ser Ser Gly Asn Met
                85                  90                  95 tct tcg gaa ctg gga cca agc tca ccg tcc                                318
Ser Ser Glu Leu Gly Pro Ser Ser Pro Ser
            100                 105

<210> SEQ ID NO 3
<211> LENGTH: 98
<212> TYPE: PRT
<213> ORGANISM: Homo sapiens

<400> SEQUENCE: 3

Gly Ser Leu Arg Leu Ser Cys Ala Ala Ser Gly Phe Thr Phe Ser Ser
         1               5                   10                  15

Tyr Ala Met Ser Trp Val Arg Gln Ala Pro Gly Lys Gly Leu Glu Trp
                    20                  25                  30

Val Ser Ala Ile Ser Gly Ser Gly Gly Ser Thr Tyr Tyr Ala Asp Ser
                    35                  40                  45

Val Lys Gly Arg Phe Thr Ile Ser Arg Asp Asn Ser Lys Asn Thr Leu
                    50                  55                  60

Tyr Leu Gln Met Asn Ser Leu Arg Ala Glu Asp Thr Ala Val Tyr Tyr
        65                  70                  75                  80
```

```
Cys Ala Lys Asp Ser Phe Arg Glu Gly Pro Trp Gly Gln Gly Thr Leu
                85                  90                  95

Val Thr

<210> SEQ ID NO 4
<211> LENGTH: 294
<212> TYPE: DNA
<213> ORGANISM: Homo sapiens
<220> FEATURE:
<221> NAME/KEY: CDS
<222> LOCATION: (1)...(294)

<400> SEQUENCE: 4 ggg tcc ctg aga ctc tcc tgt gca gcc tct gga ttc acc ttt agc agc        48
Gly Ser Leu Arg Leu Ser Cys Ala Ala Ser Gly Phe Thr Phe Ser Ser
  1               5                  10                  15 tat gcc atg agc tgg gtc cgc cag gct cca ggg aag ggg ctg gag tgg        96
Tyr Ala Met Ser Trp Val Arg Gln Ala Pro Gly Lys Gly Leu Glu Trp
             20                  25                  30 gtc tca gct att agt ggt agt ggt ggt agc aca tac tac gca gac tcc       144
Val Ser Ala Ile Ser Gly Ser Gly Gly Ser Thr Tyr Tyr Ala Asp Ser
         35                  40                  45 gtg aag ggc cgg ttc acc atc tcc aga gac aat tcc aag aac acg ctg       192
Val Lys Gly Arg Phe Thr Ile Ser Arg Asp Asn Ser Lys Asn Thr Leu
     50                  55                  60 tat ctg caa atg aac agc ctg aga gcc gag gac acg gcc gta tat tac       240
Tyr Leu Gln Met Asn Ser Leu Arg Ala Glu Asp Thr Ala Val Tyr Tyr
 65                  70                  75                  80 tgt gcg aaa gat tca ttt cgt gaa gga ccc tgg ggc cag gga acc ctg       288
Cys Ala Lys Asp Ser Phe Arg Glu Gly Pro Trp Gly Gln Gly Thr Leu
                 85                  90                  95 gtc acc                                                               294
Val Thr <210> SEQ ID NO 5
<211> LENGTH: 116
<212> TYPE: PRT
<213> ORGANISM: Homo sapiens

<400> SEQUENCE: 5

Gln Ser Ala Leu Thr Gln Pro Ala Ser Leu Ser Ala Ser Pro Gly Ala
  1               5                  10                  15

Ser Ala Ser Leu Thr Cys Thr Leu Arg Ser Gly Ile Asn Val Gly Thr
             20                  25                  30

Tyr Arg Ile Tyr Trp Tyr Gln Gln Lys Pro Gly Ser Pro Pro Gln Tyr
         35                  40                  45

Leu Leu Arg Tyr Lys Ser Asp Ser Asp Lys Gln Lys Gly Ser Gly Val
     50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Ser Ala Trp Val Phe Gly Gly Gly Thr Lys Leu
                100                 105                 110

Thr Val Leu Gly
            115

<210> SEQ ID NO 6
<211> LENGTH: 348
```

```
<212> TYPE: DNA
<213> ORGANISM: Homo sapiens
<220> FEATURE:
<221> NAME/KEY: CDS
<222> LOCATION: (1)...(348)

<400> SEQUENCE: 6 cag tct gcc ctg act cag cct gct tcc ctc tct gca tct cct gga gca      48
Gln Ser Ala Leu Thr Gln Pro Ala Ser Leu Ser Ala Ser Pro Gly Ala
 1               5                  10                  15 tca gcc agt ctc acc tgc acc ttg cgc agt ggc atc aat gtt ggt acc      96
Ser Ala Ser Leu Thr Cys Thr Leu Arg Ser Gly Ile Asn Val Gly Thr
             20                  25                  30 tac agg ata tac tgg tac cag cag aag cca ggg agt cct ccc cag tat     144
Tyr Arg Ile Tyr Trp Tyr Gln Gln Lys Pro Gly Ser Pro Pro Gln Tyr
         35                  40                  45 ctc ctg agg tac aaa tca gac tca gat aag cag aag ggc tct gga gtc     192
Leu Leu Arg Tyr Lys Ser Asp Ser Asp Lys Gln Lys Gly Ser Gly Val
     50                  55                  60 ccc agc cgc ttc tct gga tcc aaa gat gct tcg gcc aat gca ggg att     240
Pro Ser Arg Phe Ser Gly Ser Lys Asp Ala Ser Ala Asn Ala Gly Ile
 65                 70                  75                  80 tta ctc atc tct ggg ctc cag tct gag gat gag gct gac tat tac tgt     288
Leu Leu Ile Ser Gly Leu Gln Ser Glu Asp Glu Ala Asp Tyr Tyr Cys
                 85                  90                  95 atg att tgg cac agc agc gct tgg gtg ttc ggc gga ggg acc aag ctg     336
Met Ile Trp His Ser Ser Ala Trp Val Phe Gly Gly Gly Thr Lys Leu
            100                 105                 110 acc gtc cta ggt                                                      348
Thr Val Leu Gly
        115

<210> SEQ ID NO 7
<211> LENGTH: 107
<212> TYPE: PRT
<213> ORGANISM: Homo sapiens

<400> SEQUENCE: 7

Gly Ser Leu Arg Leu Ser Cys Ala Ala Ser Gly Phe Thr Phe Ser Ser
 1               5                  10                  15

Tyr Ala Met Ser Trp Val Arg Gln Ala Pro Lys Gly Leu Glu Trp
             20                  25                  30

Val Ser Ala Ile Ser Gly Ser Gly Gly Ser Thr Tyr Tyr Ala Asp Ser
         35                  40                  45

Val Lys Gly Arg Phe Thr Ile Ser Arg Asp Asn Ser Lys Asn Thr Leu
     50                  55                  60

Tyr Leu Gln Met Asn Ser Leu Arg Ala Glu Asp Thr Ala Val Tyr Tyr
 65                 70                  75                  80

Cys Ala Lys Gly Gly Ala Glu Gly Trp Tyr Glu Tyr Tyr Tyr Tyr
                 85                  90                  95

Gly Met Asp Val Trp Gly Gln Gly Thr Leu Val
            100                 105

<210> SEQ ID NO 8
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 8
```

```
ggg tcc ctg aga ctc tcc tgt gca gcc tct gga ttc acc ttt agc agc    48
Gly Ser Leu Arg Leu Ser Cys Ala Ala Ser Gly Phe Thr Phe Ser Ser
 1               5                  10                  15 tat gcc atg agc tgg gtc cgc cag gct cca ggg aag ggg ctg gag tgg    96
Tyr Ala Met Ser Trp Val Arg Gln Ala Pro Gly Lys Gly Leu Glu Trp
         20                  25                  30 gtc tca gct att agt ggt agt ggt ggt agt aca tac tac gca gac tcc   144
Val Ser Ala Ile Ser Gly Ser Gly Gly Ser Thr Tyr Tyr Ala Asp Ser
             35                  40                  45 gtg aag ggc cgg ttc acc atc tcc aga gac aat tcc aag aac acg ctg   192
Val Lys Gly Arg Phe Thr Ile Ser Arg Asp Asn Ser Lys Asn Thr Leu
     50                  55                  60 tat ctg caa atg aac agc ctg aga gcc gag gac acg gcc gta tat tac   240
Tyr Leu Gln Met Asn Ser Leu Arg Ala Glu Asp Thr Ala Val Tyr Tyr
 65                  70                  75                  80 tgt gcg aaa ggt ggg gcc gaa ggc tgg tac gag tac tac tac tac       288
Cys Ala Lys Gly Gly Ala Glu Gly Trp Tyr Glu Tyr Tyr Tyr Tyr
                 85                  90                  95 ggt atg gac gtc tgg ggc caa ggg acc ctg gtc                       321
Gly Met Asp Val Trp Gly Gln Gly Thr Leu Val
            100                 105

<210> SEQ ID NO 9
<211> LENGTH: 110
<212> TYPE: PRT
<213> ORGANISM: Homo sapiens

<400> SEQUENCE: 9

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Lys Arg Ser Ser
                 85                  90                  95

Asn Thr Leu Val Phe Gly Gly Gly Thr Lys Leu Thr Val Leu
            100                 105                 110

<210> SEQ ID NO 10
<211> LENGTH: 330
<212> TYPE: DNA
<213> ORGANISM: Homo sapiens
<220> FEATURE:
<221> NAME/KEY: CDS
<222> LOCATION: (1)...(330)

<400> SEQUENCE: 10 cag tct gcc ctg act cag cct gcc tcc gtg tct ggg tct cct gga cag    48
Gln Ser Ala Leu Thr Gln Pro Ala Ser Val Ser Gly Ser Pro Gly Gln
 1               5                  10                  15 tcg atc acc atc tcc tgc act gga acc agc agt gac gtt ggt ggt tat    96
Ser Ile Thr Ile Ser Cys Thr Gly Thr Ser Ser Asp Val Gly Gly Tyr
             20                  25                  30 aac tat gtc tcc tgg tac caa cag cac cca ggc aaa gcc ccc aaa ctc   144
Asn Tyr Val Ser Trp Tyr Gln Gln His Pro Gly Lys Ala Pro Lys Leu
```

```
atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60 tct ggc tcc aag tct ggc aac acg gcc tcc ctg acc atc tct gga ctc      240
Ser Gly Ser Lys Ser Gly Asn Thr Ala Ser Leu Thr Ile Ser Gly Leu
65                  70                  75                  80 cag gct gag gac gag gct gat tac tac tgc agc tca aaa aga agc agc      288
Gln Ala Glu Asp Glu Ala Asp Tyr Tyr Cys Ser Ser Lys Arg Ser Ser
                85                  90                  95 aac act cta gta ttc ggc gga ggg acc aag ctg acc gtc cta              330
Asn Thr Leu Val Phe Gly Gly Gly Thr Lys Leu Thr Val Leu
            100                 105                 110
```

<210> SEQ ID NO 11
<211> LENGTH: 109
<212> TYPE: PRT
<213> ORGANISM: Homo sapiens

<400> SEQUENCE: 11

```
Lys Lys Pro Gly Glu Ser Leu Arg Ile Ser Cys Lys Gly Ser Gly Tyr
1               5                   10                  15

Ser Phe Thr Thr Tyr Trp Ile Gly Trp Val Arg Gln Met Pro Gly Lys
            20                  25                  30

Gly Leu Glu Trp Met Gly Ile Ile Tyr Pro Gly Asp Ser Asp Thr Arg
        35                  40                  45

Tyr Ser Pro Ser Phe Gln Gly Gln Val Thr Ile Ser Ala Asp Thr Ser
    50                  55                  60

Ile Ser Thr Ala Tyr Leu Gln Trp Ser Ser Leu Lys Ala Ser Asp Thr
65                  70                  75                  80

Ala Ile Tyr Tyr Cys Ala Arg Glu Val Tyr Thr Gly Arg Asn Tyr Tyr
                85                  90                  95

Tyr Tyr Gly Leu Asp Val Trp Gly Gln Gly Thr Leu Val
            100                 105
```

<210> SEQ ID NO 12
<211> LENGTH: 327
<212> TYPE: DNA
<213> ORGANISM: Homo sapiens
<220> FEATURE:
<221> NAME/KEY: CDS
<222> LOCATION: (1)...(327)

<400> SEQUENCE: 12

```
aaa aag ccc ggg gag tct ctg agg atc tcc tgt aag ggc tct gga tac       48
Lys Lys Pro Gly Glu Ser Leu Arg Ile Ser Cys Lys Gly Ser Gly Tyr
1               5                   10                  15 agt ttt acc acc tac tgg atc ggc tgg gtg cgc cag atg ccc ggg aaa       96
Ser Phe Thr Thr Tyr Trp Ile Gly Trp Val Arg Gln Met Pro Gly Lys
            20                  25                  30 ggc ctg gag tgg atg ggg atc atc tat cct ggt gac tct gat acc aga      144
Gly Leu Glu Trp Met Gly Ile Ile Tyr Pro Gly Asp Ser Asp Thr Arg
        35                  40                  45 tac agc ccg tcc ttc caa ggc cag gtc acc atc tca gcc gac acg tcc      192
Tyr Ser Pro Ser Phe Gln Gly Gln Val Thr Ile Ser Ala Asp Thr Ser
    50                  55                  60 atc agt acc gcc tac ctg cag tgg agc agc ctg aag gcc tcg gac acc      240
Ile Ser Thr Ala Tyr Leu Gln Trp Ser Ser Leu Lys Ala Ser Asp Thr
65                  70                  75                  80 gcc ata tat tac tgt gcg agg gag gtc tat act ggc cga aac tac tac      288
```

-continued

```
Ala Ile Tyr Tyr Cys Ala Arg Glu Val Tyr Thr Gly Arg Asn Tyr Tyr
             85                  90                  95 tac tac ggt ctg gac gtc tgg ggc caa gga acc ctg gtc              327
Tyr Tyr Gly Leu Asp Val Trp Gly Gln Gly Thr Leu Val
            100                 105
```

NEOPLASM SPECIFIC ANTIBODIES AND USES THEREOF

CROSS-REFERENCE TO RELATED APPLICATIONS

This application is a divisional application of U.S. Ser. No. 10/520,224, filed Aug. 19, 2005, which is a 371 National Phase application of PCT/IB2003/0003487, filed Jul. 2, 2003, which claims priority from German application No. DE 102 29 906.4, filed Jul 4, 2002, Germany application No. DE 102 29 907.2, filed Jul 4, 2002, and German application No. DE 102 30 516.1, filed Jul 6, 2002.

BACKGROUND OF THE INVENTION

The present invention is related to the field of cancer diagnosis and treatment and, more specifically, to the identification of polypeptides, such as antibodies, useful in the diagnosis, detection, monitoring, and treatment of neoplasms in a mammal, e.g., a human.

In the United States well over one million individuals are diagnosed with cancer each year. Although recent advances in the medical field have significantly improved the rate of survival among cancer patients, a large number of cancer-related deaths still could be prevented by the early diagnosis of the tumor. Accordingly, at the time of initial diagnosis, an alarming number of patients have already reached late stages of the disease.

With respect to colorectal cancer, the prognosis is usually poor in 50% of all cases because the tumor is often undetected until the disease has spread and reached a terminal stage. Similarly, approximately 75% of women are diagnosed with ovarian cancer after the disease has already reached an advanced stage (stage III or IV) because the symptoms of ovarian cancer are often vague or "silent." Despite aggressive surgical intervention and new chemotherapeutic regimens, the overall 5-year survival rate for these women with advanced stage ovarian cancer has remained constant over the past 30 years, at approximately 15%. Conversely, women diagnosed with cancer confined to the ovary (stage I) have an overall 5-year survival rate approaching 90%.

Clearly, there is a need for the early and improved detection and treatment of neoplasms (e.g., stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus), as this would increase the chance of treating the neoplasm and, thereby, lead to an improved prognosis for long-term survival.

SUMMARY OF THE INVENTION

We have discovered a class of polypeptides which react with an epitope specific for neoplastic cells. These polypeptides are not only excellent diagnostic tools, but also can induce apoptosis of the neoplastic cells to which they bind. This latter characteristic results in a treatment for neoplastic diseases that lacks the side-effects of many existing therapeutics.

The present invention features polypeptides, such as monoclonal antibodies that may be used in the diagnosis and treatment of a neoplasm. Accordingly, in the first aspect, the invention features a purified polypeptide that induces apoptosis of a neoplastic cell to which it binds, but does not induce apoptosis of a non-neoplastic cell, where the antibody specifically binds to at least one of HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), or BXPC-3 (ATCC Accession No. CRL-1687) cells, and not to non-neoplastic cells.

In a second aspect, the invention features a purified polypeptide that induces apoptosis of a neoplastic cell to which it binds, but does not induce apoptosis of a non-neoplastic cell, where the polypeptide specifically binds to a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus cell and not to a non-neoplastic cell.

In the third aspect, the invention features a purified polypeptide that inhibits cell proliferation when bound to a neoplastic cell, but does not inhibit cell proliferation of a non-neoplastic cell, where the polypeptide specifically binds to at least one of HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), or BXPC-3 (ATCC Accession No. CRL-1687) cells, and not to non-neoplastic cells.

In a desirable embodiment of the first and third aspects of the invention, the polypeptide binds to ASPC-1 (ATCC Accession No. CRL-1682) and BXPC-3 (ATCC Accession No. CRL-1687) cells and not to non-neoplastic cells, and the neoplastic cell is a stomach adenocarcinoma, colorectal adenocarcinoma, squamous cell lung carcinoma, lung adenocarcinoma, squamous cell carcinoma of the esophagus, adenocarcinoma of the pancreas, adenocarcinoma of the prostate, ductal carcinoma of the breast, lobular carcinoma of the breast, adenocarcinoma of the ovary, or adenocarcinoma of the uterus cell. In addition, the polypeptide may include the sequence of SEQ ID NO:1 or 3, or a sequence that is substantially identical to the sequence of SEQ ID NO:1 or 3. Furthermore, the polypeptide also may be produced by the PM-1 cell line deposited at the DSMZ under Accession No. DSM ACC2599.

In another desirable embodiment of the first and third aspects, the polypeptide binds to HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), and BXPC-3 (ATCC Accession No. CRL-1687) cells and not to non-neoplastic cells, and the neoplastic cell is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, or adenocarcinoma of the uterus cell. In addition, the polypeptide may include the sequence of SEQ ID NO:5 or 7, or a sequence that is substantially identical to the sequence of SEQ ID NO:5 or 7. Furthermore, the polypeptide also may be produced by the PM-2 cell line deposited at the DSMZ under Accession No. DSM ACC2600.

In a further desirable embodiment of the first and third aspects, the polypeptide binds to CACO-2 (ATCC Accession No. HBT-37; DSMZ Accession No. ACC 169) and COLO-206F (DSMZ Accession No. ACC 21) cells and not to non-neoplastic cells, and the neoplastic cell is a colorectal adenocarcinoma or adenocarcinoma of the endometrium cell. In addition, the polypeptide may include the sequence of SEQ ID NO:9 or 11, or a sequence that is substantially identical to the sequence of SEQ ID NO:9 or 11. Furthermore, the polypeptide also may be produced by the CM-2 cell line deposited at the DSMZ under Accession No. DSM ACC2598.

The fourth aspect of the invention features a purified polypeptide that inhibits cell proliferation when bound to a neoplastic cell, but does not inhibit cell proliferation of a non-neoplastic cell, where the polypeptide specifically binds to a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus cell and not to a non-neoplastic cell.

In desirable embodiments of the first four aspects of the invention, the polypeptide includes an antibody or a functional fragment thereof. For example, the functional fragment may be selected from the group consisting of $V_L$, $V_H$, $F_V$, $F_C$, Fab, Fab', and $F(ab')_2$. In addition, the functional fragment may include a fragment that is substantially identical to the sequence of SEQ ID NOS:1, 3, 5, 7, 9, or 11 or may include a fragment of the sequence of SEQ ID NO:1, 3, 5, 7, 9, or 11. In addition, the fragment may be substantially identical to a polypeptide including amino acids 26-31, 49-51, and 88-95 of SEQ ID NO:1 or amino acids 11-18, 36-43, and 82-90 of SEQ ID NO:3; a polypeptide including amino acids 26-34, 52-58, and 97-103 of SEQ ID NO:5 or amino acids 1'-18, 36-43, and 82-100 of SEQ ID NO:7; or a polypeptide including amino acids 26-34, 51-54, and 91-99 of SEQ ID NO:9 or amino acids 16-22, 40-47, and 86-100 of SEQ ID NO:11.

The fifth aspect of the invention features a purified polypeptide that includes the amino acid sequence of SEQ ID NO:1; the sixth aspect of the invention features a purified polypeptide that includes the amino acid sequence of SEQ ID NO:3; the seventh aspect of the invention features a purified polypeptide that includes the amino acid sequence of SEQ ID NO:5; the eighth aspect of the invention features a purified polypeptide that includes the amino acid sequence of SEQ ID NO:7; the ninth aspect of the invention features a purified polypeptide that includes the amino acid sequence of SEQ ID NO:9; and the tenth aspect of the invention features a purified polypeptide that includes the amino acid sequence of SEQ ID NO:11.

Furthermore, the invention features a purified polypeptide including amino acid 26-31, 49-51, and 88-95 of SEQ ID NO:1, a purified polypeptide including amino acids 11-18, 36-43, and 82-90 of SEQ ID NO:3, a purified polypeptide including amino acids 26-34, 52-58, and 97-103 of SEQ ID NO:5, a purified polypeptide including amino acids 11-18, 36-43, and 82-100 of SEQ ID NO:7, a purified polypeptide including amino acids 26-34, 51-54, and 91-99 of SEQ ID NO:9, and a purified polypeptide including amino acids 16-22, 40-47, and 86-100 of SEQ ID NO:11. Moreover, the invention features a purified polypeptide including amino acid 26-31, 49-51, and 88-95 of SEQ ID NO:1 and amino acids 11-18, 36-43, and 82-90 of SEQ ID NO:3, a purified polypeptide including amino acids 26-34, 52-58, and 97-103 of SEQ ID NO:5 and amino acids 11-18, 36-43, and 82-100 of SEQ ID NO:7, and a purified polypeptide including amino acids 26-34, 51-54, and 91-99 of SEQ ID NO:9 and amino acids 16-22, 40-47, and 86-100 of SEQ ID NO:11.

In an eleventh aspect, the invention features a purified polypeptide that includes the amino acid sequence of SEQ ID NOS:1 and 3; in a twelfth aspect, the invention features a purified polypeptide that includes the amino acid sequence of SEQ ID NOS:5 and 7; and in a thirteenth aspect, the invention features a purified polypeptide that includes the amino acid sequence of SEQ ID NOS:9 and 11.

In a desirable embodiment of the first thirteen aspects of the invention, the polypeptide is an antibody, such as a monoclonal antibody, e.g., a human monoclonal antibody.

In a fourteenth aspect, the invention features a cell that expresses the polypeptide of the first or second aspect and in a fifteenth aspect, the invention features a cell that expresses the polypeptide of the third or fourth aspect of the invention. In the sixteenth aspect, the invention features a cell that expresses a polypeptide that includes a sequence that is substantially identical to the amino acid sequence of SEQ ID NO:1 or 3, and in desirable embodiments of this aspect, the polypeptide includes the sequence of SEQ ID NO:1 or 3, or both SEQ ID NO:1 and 3.

In a seventeenth aspect, the invention features a cell that expresses a polypeptide that includes a sequence that is substantially identical to the amino acid sequence of SEQ ID NO:5 or 7, and in desirable embodiments of this aspect, the polypeptide includes the sequence of SEQ ID NO:5 or 7, or both SEQ ID NO:5 and 7.

In an eighteenth aspect, the invention features a cell that expresses a polypeptide that includes a sequence that is substantially identical to the amino acid sequence of SEQ ID NO:9 or 11, and in desirable embodiments of this aspect, the polypeptide includes the sequence of SEQ ID NO:9 or 11, or both SEQ ID NO:9 and 11. In further desirable embodiments of the fourteenth through eighteenth aspects of the invention, the cell is a hybridoma.

In the nineteenth aspect, the invention features a method of generating the cell of the fourteenth aspect. This method involves the steps of: (a) contacting lymphocytes with a heteromyeloma cell line under conditions that result in the fusion of a lymphocyte with a heteromyeloma cell, where the fusion results in a hybridoma, (b) determining whether the hybridoma produces a polypeptide that induces apoptosis of a neoplastic cell to which it binds, but does not induce apoptosis of a non-neoplastic cell, and (c) determining whether the hybridoma produces a polypeptide that specifically binds to at least one of HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), or BXPC-3 (ATCC Accession No. CRL-1687) cells and not to non-neoplastic cells.

In the twentieth aspect, the invention features a method of generating the cell of the fifteenth aspect. This method involves the steps of: (a) contacting lymphocytes with a heteromyeloma cell line under conditions that result in the fusion of a lymphocyte with a heteromyeloma cell, where the fusion results in a hybridoma, (b) determining whether the hybridoma produces a polypeptide that inhibits proliferation in a neoplastic cell to which it binds, but does not inhibit proliferation in a non-neoplastic cell, and (c) determining whether the hybridoma produces a polypeptide that specifically binds to at least one of HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), or BXPC-3 (ATCC Accession No. CRL-1687) cells and not to non-neoplastic cells.

In a twenty-first aspect, the invention features a use of the purified polypeptide of any one of the first thirteen aspects of the invention in a method of diagnosing a neoplasm in a mammal, e.g., a human. This method involves the steps of: (a) contacting a cell or tissue sample of the mammal with the purified polypeptide of any one of the first thirteen aspects of the invention, and (b) detecting whether the purified polypeptide binds to the cell or tissue sample, where binding of the purified polypeptide to the cell or tissue sample is indicative of the mammal having a neoplasm.

In desirable embodiments of the twenty-first aspect of the invention, the neoplasm is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Further, the polypeptide may be conjugated to a protein purification tag, e.g., a cleavable protein purification tag.

In the twenty-second aspect, the invention features a use of the purified polypeptide of any one of the first thirteen aspects of the invention in a method of treating a proliferative disorder in a mammal, e.g., a human. This method involves the step of contacting a cell or tissue sample with the purified polypeptide of any one of the first thirteen aspects, where binding of the purified polypeptide to the cell or tissue sample results in the induction of apoptosis of the cell or tissue sample.

In desirable embodiments of the twenty-second aspect of the invention, the proliferative disorder is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Desirably, the detectable agent is capable of inducing apoptosis of the cell or tissue sample. In addition, the polypeptide may be conjugated to a protein purification tag, e.g., a protein purification tag that is cleavable.

In the twenty-third aspect, the invention features a use of the purified polypeptide of any one of the first thirteen aspects of the invention in a method of treating a proliferative disorder in a mammal, e.g., a human. This method involves the step of contacting a cell or tissue sample with the purified polypeptide of any one of the first thirteen aspects of the invention, where binding of the purified polypeptide to the cell or tissue sample results in a reduction in proliferation of the cell or of a cell in the tissue sample.

In desirable embodiments of the twenty-third aspect of the invention, the proliferative disorder is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus. In further desirable embodiments of this aspect, the polypeptide is an antibody or the polypeptide is conjugated to a detectable, agent selected from the group consisting of a radionuclide, a fluorescent marker, an enzyme, a cytotoxin, a cytokine, and a growth inhibitor. Desirably, the detectable agent is capable of inhibiting cell proliferation of the cell or tissue sample. In addition, the polypeptide may be conjugated to a protein purification tag, e.g., a protein purification tag that is cleavable.

In a twenty-fourth aspect, the invention features a medicament that contains the purified polypeptide of any one of the first thirteen aspects of the invention in a pharmaceutically acceptable carrier.

In the twenty-fifth aspect, the invention features a diagnostic agent that contains the purified polypeptide of any one of the first thirteen aspects of the invention.

In the twenty-sixth aspect, the invention features an isolated nucleic acid molecule that is substantially identical to the sequence of SEQ ID NO:2, 4, 6, 8, 10, or 12, and in the twenty-seventh aspect, the invention features an isolated nucleic acid sequence that hybridizes under high stringency conditions to the sequence of SEQ ID NO:2, 4, 6, 8, 10, or 12.

In the twenty-eighth aspect, the invention features an isolated nucleic acid molecule that includes the sequence of SEQ ID NO:2, 4, 6, 8, 10, or 12; in the twenty-ninth aspect, the invention features an isolated nucleic acid molecule that includes sequences that are substantially identical to nucleotides 76-93, 145-153, and 262-285 of SEQ ID NO:2. In a desirable embodiment of this aspect, the isolated nucleic acid molecule includes nucleotides 76-93, 145-153, and 262-285 of SEQ ID NO:2.

The thirtieth aspect of the invention features an isolated nucleic acid molecule that includes sequences that are substantially identical to nucleotides 31-54, 106-129, and 244-270 of SEQ ID NO:4. In a desirable embodiment of this aspect, the isolated nucleic acid molecule includes nucleotides 31-54, 106-129, and 244-270 of SEQ ID NO:4

In the thirty-first aspect, the invention features an isolated nucleic acid molecule that includes sequences that are substantially identical to nucleotides 76-102, 154-174, and 289-309 of SEQ ID NO:6. In a desirable embodiment of this aspect, the isolated nucleic acid molecule includes nucleotides 76-102, 154-174, and 289-309 of SEQ ID NO:6.

In the thirty-second aspect, the invention features an isolated nucleic acid molecule that includes sequences that are substantially identical to nucleotides 31-54, 106-129, and 244-300 of SEQ ID NO:8. In a desirable embodiment of this aspect, the isolated nucleic acid molecule includes nucleotides 31-54, 106-129, and 244-300 of SEQ ID NO:8

In the thirty-third aspect, the invention features an isolated nucleic acid molecule that includes sequences that are substantially identical to nucleotides 76-102, 151-162, and 271-297 of SEQ ID NO:10. In a desirable embodiment of this aspect, the isolated nucleic acid molecule includes nucleotides 76-102, 151-162, and 271-297 of SEQ ID NO:10.

In the thirty-fourth aspect, the invention features an isolated nucleic acid molecule that includes sequences that are substantially identical to nucleotides 46-66, 118-141, and 256-300 of SEQ ID NO:12. In a desirable embodiment of this aspect, the isolated nucleic acid molecule includes nucleotides 46-66, 118-141, and 256-300 of SEQ ID NO:12.

In the thirty-fifth aspect, the invention features a vector including the nucleic acid molecule of any one of that twenty-sixth through thirty-fourth aspects of the invention, and in the thirty-sixth aspect, the invention features a cell that includes the vector of the thirty-fifth aspect.

The thirty-seventh aspect of the invention features a method of preparing the purified polypeptide of the first four aspects of the invention. This method involves contacting a cell with the vector of the thirty-fifth aspect of the invention and isolating the polypeptide expressed by the cell.

DEFINITIONS

By "detectable agent" is meant a compound that is linked to a diagnostic agent to facilitate detection. Such a "detectable agent" may be covalently or non-covalently linked to a diagnostic agent. In addition, the linkage may be direct or indirect. Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

By a "diagnostic agent" is meant a compound that may be used to detect a neoplastic cell by employing any one of the assays described herein as well as any other method that is standard in the art. A diagnostic agent may include, for example, an antibody which specifically binds to at least one of the following cells: HT-29 (ATCC Accession No. HTB-38; DSMZ Accession No. ACC 299), CACO-2 (ATCC Accession No. HBT-37; DSMZ Accession No. ACC 169), COLO-320 (DSMZ Accession No. ACC 144), COLO-206F (DSMZ Accession No. ACC 21), ASPC-1 (ATCC Accession No. CRL-1682), and BXPC-3 (ATCC Accession No. CRL-1687), but not to non-neoplastic cells. In addition, a "diagnostic agent" may inhibit cell proliferation, induce apoptosis, or both only when it is bound to a neoplastic cell, but not a non-neoplastic cell.

Examples of neoplastic cells that may be detected with such a "diagnostic agent" include stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus cells. Moreover, a "diagnostic agent" may include, for example, peptides, polypeptides, synthetic organic molecules, naturally-occurring organic molecules, nucleic acid molecules, and components thereof, as well as one or more detectable agent covalently or non-covalently linked to the diagnostic agent.

By a "functional fragment," as used herein in reference to polypeptide, is meant a fragment that retains at least one biological activity of the full-length polypeptide. Examples of such a biological activity are the ability to specifically bind an antigen, induce apoptosis, and/or inhibit cell proliferation. These biological activities may be determined, for example, using any one of the assays described herein.

Examples of functional fragments of an antibody are $V_L$, $V_H$, $F_V$, $F_C$, Fab, Fab', or F(ab')$_2$ fragments (see, e.g., Huston et al., Cell Biophys. 22:189-224, 1993; and Harlow and Lane, Antibodies: A Laboratory Manual, Cold Spring Harbor Laboratory, 1988). Desirably, a "functional fragment" has an amino acid sequence that is substantially identical to a fragment, e.g., 3, 4, 5, 10, 15, 20, 15, 30, 50, 75, or 100 contiguous amino acids, of the amino acid sequence of SEQ ID NO:1, 3, 5, 7, 9, or 11. In more desirable embodiments, a "functional fragment" is identical to a fragment of the sequence of SEQ ID NO:1, 3, 5, 7, 9, or 11. Such a "functional fragment" may contain 3, 4, 5, 10, 15, 20, 15, 30, 50, 75, or 100 contiguous amino acids of SEQ ID NO:1, 3, 5, 7, 9, or 11, or may be the entire amino acid sequence of SEQ ID NO:1, 3, 5, 7, 9, or 11. In desirable embodiments, such a fragment includes one or more of the Complement Determining Regions (CDR) of the $V_H$ or the $V_L$ regions of the PM-1, PM-2, or CM-2 antibody. For example, a functional fragment may include amino acids 26-31, 49-51, and/or 88-95 of SEQ ID NO:1; amino acids 11-18, 36-43 and/or 82-90 of SEQ ID NO:3; amino acids 26-34, 52-58, and/or 97-103 of SEQ ID NO:5; amino acids 11-18, 36-43, and/or 82-100 of SEQ ID NO:7; amino acids 26-34, 51-54, and/or 91-99 of SEQ ID NO:9; or amino acids 16-22, 40-47, and/or 86-100 of SEQ ID NO:11.

By "high stringency hybridization conditions" is meant, for example, hybridization at approximately 42° C. in about 50% formamide, 0.1 mg/ml sheared salmon sperm DNA, 1% SDS, 2×SSC, 10% Dextran Sulfate, a first wash at approximately 65° C. in about 2×SSC, 1% SDS, followed by a second wash at approximately 65° C. in about 0.1×SSC. Alternatively, "high stringency hybridization conditions" may include hybridization at approximately 42° C. in about 50% formamide, 0.1 mg/ml sheared salmon sperm DNA, 0.5% SDS, 5×SSPE, 1×Denhardt's, followed by two washes at room temperature in 2×SSC, 0.1% SDS, and two washes at between 55-60° C. in 0.2×SSC, 0.1% SDS.

A "hybridoma," as used herein, is any cell that is artificially created by the fusion of a normal cell such as an activated lymphocyte with a neoplastic cell, e.g., a myeloma. The hybrid cell, which results from the fusion of at least two cells, may produce a monoclonal antibody or T cell product identical to those produced by the immunologically-competent parent. In addition, these cells, like the neoplastic parent, are immortal.

"Inhibiting cell proliferation," as used herein, refers to a reduction in the rate of cell division of a cell in comparison with the normal rate of cell division of that type of cell. Inhibition of cell proliferation may be assayed using a number of methods standard in the art, for example, the MTT cell proliferation assay described herein, BrdU incorporation, and $^3$H thymidine uptake. Such assays are described, for example, in Ausubel et al., Current Protocols in Molecular Biology, Wiley Interscience, New York, 2001; and Sambrook et al., Molecular Cloning: A Laboratory Manual, Cold Spring Harbor Laboratory, N.Y., 1989. Desirably, the inhibition of cell proliferation is 20%, 40%, 50%, or 75%. In desirable embodiments, the inhibition of cell proliferation is 80%, 90%, 95%, or even a complete inhibition of cell proliferation.

"Inducing apoptosis," as used herein, refers to the appearance of characteristics in a cell that are well defined in the art (see, e.g., Wyllie et al., Br. J. Cancer 80 Suppl. 1:34-37, 1999; Kerr et al., Br. J. Cancer 26:239-257, 1972). These characteristics include morphological characteristics, such as membrane blebbing, DNA condensation, as well as changes in F-actin content, mitochondrial mass, and membrane potential. The induction of apoptosis may be assayed using a number of methods standard in the art, for example, a cell death ELISA, TUNEL staining, DNA stains, e.g., Hoechst 33258, and staining with various vital dyes such as acridine orange, Mito Tracker Red® staining (Molecular Probes, Eugene, Oreg.), and Annexin V® staining (Becton Dickinson, NJ). As used herein "inducing apoptosis" refers to an increase in the number of cells undergoing apoptosis when compared with a control cell population. For instance, the increase of apoptosis may be 10%, 20%, 40%, 50%, or 75%. In desirable embodiments, the induction of apoptosis results in an increase of apoptosis that is 2-fold, 3-fold, 10-fold, or even 100-fold over that seen in a control cell population.

A "neoplastic cell," as used herein, refers to a cell which is undergoing cell division, not undergoing apoptosis, or both, under inappropriate conditions. For example, a "neoplastic cell" may undergo cell division when a corresponding non-neoplastic cell does not undergo cell division, or, alternatively, a "neoplastic cell" may not respond to normal cell-cycle checkpoint controls.

A "proliferative disease," as used herein, refers to any disorder that results in the abnormal proliferation of a cell. Specific examples of proliferative diseases are various types of neoplasms, such as stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus. However, proliferative diseases may also be the result of the cell becoming infected with a transforming virus.

A "protein purification tag," as used herein, is a peptide, e.g., an epitope tag, that is covalently or non-covalently added to a protein to aid in the purification of the protein. Desirably such peptides bind with high affinity to an antibody or to another peptide such as biotin or avidin. Commercially available examples of epitope tags include His-tags, HA-tags, FLAG™-tags, and c-Myc-tags. However, any epitope that is recognized by an antibody also may be used as a protein purification tag. See, for example, Ausubel et al., *Current Protocols in Molecular Biology*, Wiley Interscience, New York, 2001; and Sambrook et al., *Molecular Cloning: A Laboratory Manual*, Cold Spring Harbor Laboratory, N.Y., (1989). Protein purification tags may be cleaved from a protein, for example, by using an enzyme, e.g., thrombin, or a chemical, e.g., cyanogen bromide.

By "specifically recognize," as used herein in reference to a polypeptide, e.g., an antibody, is meant an increased affinity of a polypeptide for a particular protein, e.g., an antigen, relative to an equal amount of any other protein. For example, an antibody, e.g., the PM-1, PM-2, or CM-2 human monoclonal antibody, that specifically binds to HT-29 (American Type Culture Collection ("ATCC") Accession No. HTB-38, German Collection of Microorganisms and Cell Cultures ("DSMZ") Accession No. ACC 299), CACO-2 (ATCC Accession No. HBT-37, DSMZ Accession No. ACC 169), COLO-320 (DSMZ Accession No. ACC 144), COLO-206F (DSMZ Accession No. ACC 21), ASPC-1 (ATCC Accession No. CRL-1682), or BXPC-3 (ATCC Accession No. CRL-1687) cells desirably has an affinity for its antigen that is at least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, or co-immunoprecipitation.

By "substantially identical" is meant a polypeptide or nucleic acid exhibiting at least 50%, 75%, 80%, 85%, or 90% identity to a reference amino acid (e.g., the sequence of SEQ ID NO:1, 3, 5, 7, 9, or 11) or nucleic acid sequence (e.g., the sequence of SEQ ID NO:2, 4, 6, 8, 10, or 12), or a fragment thereof. In desirable embodiments, the polypeptide or nucleic acid sequence is at least 95%, 98%, 99%, or even 100% identical to a reference amino acid or nucleic acid sequence. For polypeptides, the length of comparison sequences will generally be at least 3, 4, 5, 6, 8, 10, or 15 amino acids and desirably at least 20 or 25 contiguous amino acids. In more desirable embodiments, the length of comparison sequences is at least 30, 50, 75, 90, 95, or 100 contiguous amino acids, or even the full-length amino acid sequence. For nucleic acids, the length of comparison sequences will generally be at least 9, 10, 15, 20, or 25 contiguous nucleotides, and desirably at least 30 contiguous nucleotides. In more desirable embodiments, the length of comparison sequences is at least 50, 75, 150, 225, 270, 285, or 300 contiguous nucleotides, or even the full-length nucleotide sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "purified" or "isolated" is meant separated from other components that naturally accompany it. Typically, a factor is substantially pure when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule in the genome of an organism. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al. (*Current Protocols in Molecular Biology*, Wiley Interscience, New York, 2001). The factor is desirably at least 2, 5, or 10 times as pure as the starting material, as measured using polyacrylamide gel electrophoresis, column chromatography, optical density, HPLC analysis, or Western analysis (Ausubel et al., *Current Protocols in Molecular Biology*, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

Other features and advantages of the invention will be apparent from the following Detailed Description, the Drawings, and the Claims.

BRIEF DESCRIPTION OF THE DRAWINGS

FIG. 1A shows staining of an adenocarcinoma of the pancreas; FIG. 1B shows staining of a squamous cell carcinoma of the lung; FIG. 1C shows staining of an adenocarcinoma of the pancreas; and FIG. 1D shows staining of an invasive ductal carcinoma of the breast. The original magnification for these images was 200×.

FIG. 3A shows the concentration dependent inhibition of cell proliferation with antibodies PM-1 and PM-2 on pancreas carcinoma cell line BXPC-3. FIG. 3B shows the concentration dependent inhibition of cell proliferation with antibody CM-2 on colon carcinoma cell line Colo-206F. The control for these experiments was depleted cell culture supernatant with an unrelated IgM antibodies added at similar concentrations.

FIG. 4A shows PM-1 and PM-2 monoclonal antibody-induced apoptosis of pancreas adenocarcinoma cell line BXPC-3. FIG. 4B shows CM-2 monoclonal antibody-induced apoptosis of Colon adenocarcinoma cell line CACO-2. The control in these experiments was depleted cell culture supernatant at a similar concentration.

FIG. 5A shows a Western blot of a membrane extract of pancreas carcinoma cell line BXPC-3. Here, antibody PM-1 recognizes two main bands of about 35 and 65 kDa. FIG. 5B shows a Western blot of the same cell line as used in FIG. 5A, but here the blot was incubated with the PM-2 antibody. The PM-2 antibody recognizes two bands with molecular weights of approximately 55 and 115 kDa. FIG. 5C shows a Western blot of membrane extracts of colon carcinoma cell line CACO2 incubated with the CM-2 antibody. The CM-2 antibody reacts with proteins in the range of 40 to 50 kDa. As a control in these experiments, unrelated human IgM was added at a similar concentration to rule out non-specific binding.

FIG. 12 is the amino acid sequence (SEQ ID NO:1) and the nucleic acid sequence (SEQ ID NO:2) of the variable region of the light chain of human monoclonal antibody PM-1. Complement Determining Regions (CDR) 1-3 also are shown.

FIG. 13 is the amino acid sequence (SEQ ID NO:3) and the nucleic acid sequence (SEQ ID NO:4) of the variable region of the heavy chain of human monoclonal antibody PM-1. CDR1-3 also are shown.

FIG. 14 is the amino acid sequence (SEQ ID NO:5) and the nucleic acid sequence (SEQ ID NO:6) of the variable region of the light chain of human monoclonal antibody PM-2. CDR1-3 also are shown.

FIG. 15 is the amino acid sequence (SEQ ID NO:7) and the nucleic acid sequence (SEQ ID NO:8) of the variable region of the heavy chain of human monoclonal antibody PM-2. CDR1-3 also are shown.

FIG. 16 is the amino acid sequence (SEQ ID NO:9) and the nucleic acid sequence (SEQ ID NO:10) of the variable region of the light chain of human monoclonal antibody CM-2. CDR1-3 also are shown.

FIG. 17 is the amino acid sequence (SEQ ID NO:11) and the nucleic acid sequence (SEQ ID NO:12) of the variable region of the heavy chain of human monoclonal antibody CM-2. CDR1-3 also are shown.

DETAILED DESCRIPTION

Figure 1:
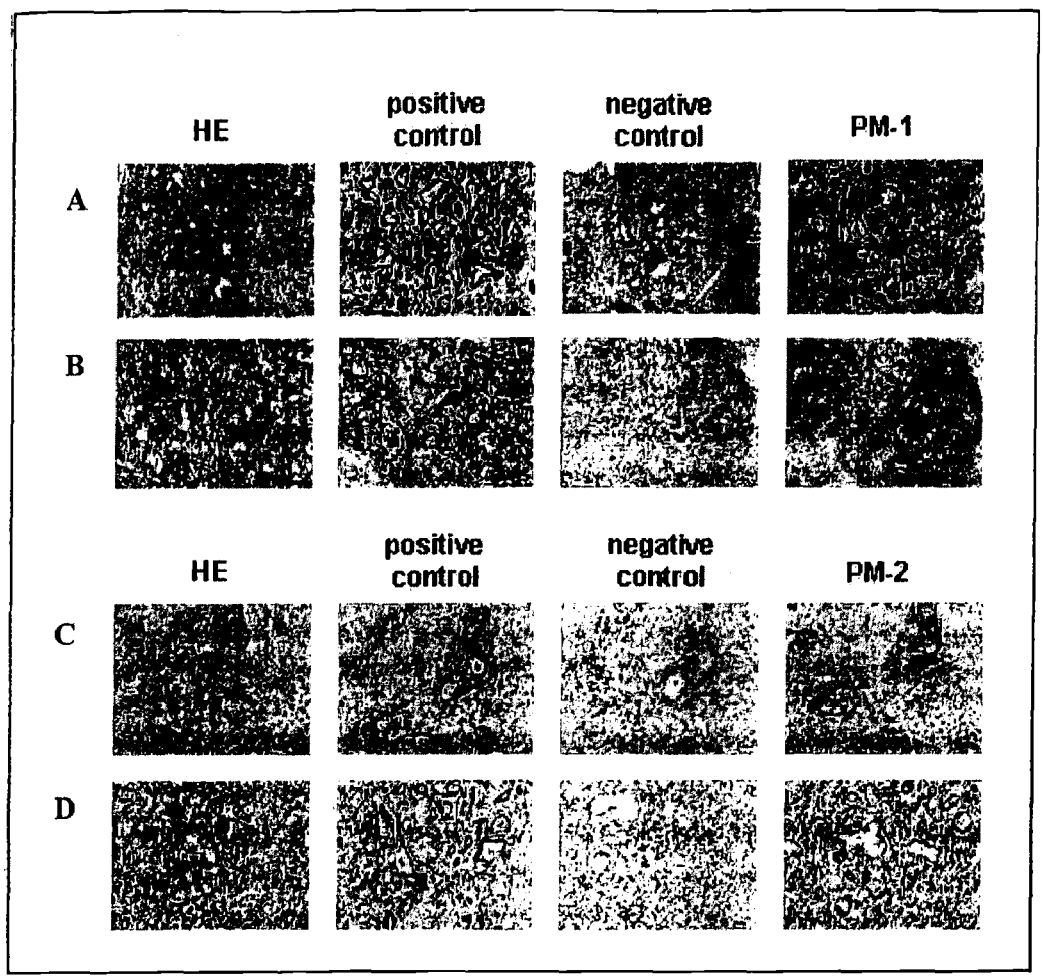
FIGS. 1A-1D are a series of images showing immunohistochemical staining of PM-1 and PM-2 on different carcinomas. Paraffin sections were stained with hematoxylin-eosin, positive control antibodies (CK7 for adenocarcinoma of the pancreas, CK5/6 for squamous cell carcinoma of the lung, and CK8 for invasive ductal adenocarcinoma of the breast), secondary antibody alone as a negative control, and either antibody PM-1 or PM-2.

The present invention features polypeptides, such as antibodies, and their use in the treatment and diagnosis of neoplasms. We have characterized several human monoclonal antibodies (PM-1, PM-2, and CM-2) that specifically recognize a number of carcinomas. Not only do these monoclonal antibodies recognize these neoplasms, but, upon binding to a cell, they can induce apoptosis of neoplastic cells, inhibit their proliferation, or even both. Thus, the PM-1, PM-2, and CM-2 monoclonal antibodies, and other antibodies, or fragments thereof, that are specific for the antigen recognized by these antibodies, may be used in a variety of methods for diagnosing and treating a neoplasm.

The cell lines that produce the human PM-1, PM-2, and CM-2 monoclonal antibodies were deposited on Jul. 2, 2003 at the German Collection of Microorganisms and Cell Cultures ("DSMZ"—Deutsche Sammlung von Mikroorganismen und Zellkulturen GmbH, Mascheroder Weg 1b, 38124 Braunschweig, Germany) under the terms of the Budapest Treaty.

Antibodies and Polypeptides

Antibodies play an essential role in maintaining the health of an individual. In particular, antibodies are present in serum and bind to and help eliminate diverse pathogens such as bacteria, viruses, and toxins. Antibodies consist of Y-shaped protein structures built from two heavy chains and two light chains. Each chain has a modular construction: each light chain consists of two domains, and each heavy chain has at least four domains. The antigen binding site is fashioned by one domain from the heavy chain ($V_H$ domain) and one domain from the light chain ($V_L$ domain). Indeed, small antigen binding fragments can be prepared by linking these two domains, either associated non-covalently, or covalently via disulphide bonds or a peptide linker. The antigen binding domains are more variable in amino acid sequence than the other domains of the antibody, and are therefore termed variable (V) domains, in contrast to the constant (C) domains. The constant domains of the antibody are responsible for triggering antibody effector mechanisms, such as complement lysis and cell-mediated killing.

Antibodies are made by B-lymphocytes in a process involving gene rearrangement. During the development of these cells, the genes encoding the variable domains are assembled from genetic elements. In the case of the $V_H$ domains there are three elements, the un-rearranged $V_H$ gene, D segment, and $J_H$ segment. In the case of the $V_L$ domains, there are two elements, the un-rearranged $V_L$ (V Lambda or V Kappa) gene and the $J_L$ (J Lambda or J Kappa) segment. Random combination of these gene segments and random combination of the rearranged $V_H$ and $V_L$ domains generate a large repertoire of antibodies, capable of binding to a large diversity of equally diverse antigens. Further, the $V_H$ and $V_L$ regions each have three Complement Determining Regions (CDR) and four framework regions (FR). The FRs are the backbone of the antibody and the CDRs are the parts of the antibody that bind the antigen. One skilled in the art can determine the FR and CDR regions of an antibody by comparing the amino acid sequence of a number of antibodies raised in the same species.

In general, the presently claimed polypeptide is any agent that binds to any one of HT-29, CACO-2, COLO-320, COLO-206F, ASPC-1, or BXPC-3, but does not bind to non-neoplastic cells. The polypeptide may be an antibody, such as a human monoclonal antibody (e.g., PM-1, PM-2, or CM-2), or a functional fragment thereof. Overall, the polypeptide of the invention can exclusively bind to both neoplastic tissues and neoplastic cells, but not to non-neoplastic tissue or cells. The polypeptide also may induce apoptosis of a neoplastic cell to which it binds, but not in a non-neoplastic cell, or, alternatively, the polypeptide may inhibit proliferation of the neoplastic cell it binds to, but not in a non-neoplastic cell. Desirably, the polypeptide can simultaneously induce apoptosis and inhibit proliferation of neoplastic cells, but not of non-neoplastic cells. Such a polypeptide is, therefore, useful for the detection, monitoring, prevention, and treatment of cancers in mammals. Exemplary cancers amenable to the methods of the current invention include colorectal cancer, ovarian carcinoma, squamous cell lung carcinoma, small cell lung carcinoma, lobular and ductal mammary carcinomas, melanoma, breast cancer, lung cancer, such as lung adenocarcinomas, gastric cancer, pancreatic cancer, such as pancreatic adenocarcinomas, glioma, sarcomas, gastrointestinal cancer, brain tumor, esophageal cancer, such as esophagial squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias. Such polypeptides are particularly useful for the detection and treatment of a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, or adenocarcinoma of the uterus.

Production

The polypeptides according to the claimed invention can be produced by any method known in the art for small scale, large scale, or commercial production of polypeptides. For example, monoclonal antibodies, such as PM-1, PM-2, and CM-2, may be produced by hybridoma cell lines. Such cell lines are typically generated by the fusion of spleen and lymph node lymphocytes derived from patients having a neoplasm, such as colon carcinoma or a pancreatic carcinoma, with a heteromyeloma cell line. Exemplary heteromyeloma cell lines include, for example, HAB-1 (Vollmers et al, Cancer 74:1525-1532, 1994), CB-F7 (Delvig et al., Hum. Antibodies Hybridomas 6:42-46, 1995), K6H6B5 (Delvig et al., Hum. Antibodies Hybridomas 6:42-46, 1995), H7NS.934 (Delvig et al., Hum. Antibodies Hybridomas 6:42-46, 1995), SHM-D33 (Bron et al., Proc. Natl. Acad. Sci. USA 81:3214-3217, 1984), and B6B11 (Borisova et al., Vopr. Virusol. 44:172-174, 1999). The ability to generate human monoclonal antibodies from lymphocytes of cancer patients allows the isolation of antibodies that are generated by an immune response in the cancer patient to the tumor.

Typically, portions of the lymph nodes or spleen are surgically removed from a patient having cancer, such as colon carcinoma or a pancreatic carcinoma. Lymphocytes may be prepared as cell suspensions by mechanical means and subsequently fused at, for example, a 1:2 or 1:3 ratio with a heteromyeloma cell line under conditions that result in cell fusion. For instance, the heteromyeloma cell line HAB-1, which is generated by the fusion of a human lymphocyte with the mouse myeloma NS-0, may be used for this purpose. A proportion of lymphocytes isolated from the cancer patient may also be maintained in culture. These cells serve as a source of human autologous cells useful for the initial antibody screening described below.

Following the fusion of the lymphocytes derived from the cancer patient with the heteromyeloma cell line, an antibody producing hybridoma or trioma is generated. Once constructed, hybridomas are generally stable in growth and antibody production in standard and mass cultures (flasks, miniPerm, fermenters, etc.) for several months. Levels of antibody production typically range between 0.01-0.1 mg/mL in flasks and between 0.1-0.5 mg/mL in miniPerm. Cell fusion may be achieved by any method known in the art, and includes, for example, the use of 40% polyethylene glycol. Hybridomas may be cultured in media containing HAT (Hypovanthin-aminopterin-thymidin) and after four weeks, supernatants may be screened for antibody production using an ELISA assay. Positive clones may then be tested in attachment inhibition and binding assays using autologous cell lines as prepared above. Positive clones further may be tested using immunoperoxidase staining of tumor and normal tissues. Thus, clones may be selected on the basis of their reactivity with autologous and allogeneic neoplastic cells. The antibody may be purified from mass cultures with use of cation-exchange chromatography followed by gel filtration as described, for example, by Vollmers et al. (Oncology Reports 5:35-40, 1998). Following the production of antibodies, additional functional and immunohistochemical tests of the antibodies produced by the trioma may be performed. For example, the antibodies produced by the hybridoma can be tested for their ability to induce apoptosis, inhibit cellular proliferation, or both, relative to untreated control cells. The antibodies can also be tested for their ability to specifically bind the neoplastic cell lines HT-29, CACO-2, COLO-320, COLO-206F, ASPC-1, or BXCP-3, relative to non-neoplastic cells.

Alternatively, the polypeptide, including an antibody, or a fragment thereof, may be produced by the expression of the polypeptide or antibody in a host cell such as *E. coli* or yeast, e.g., *S. cerevisiae*, or a mammalian cell line. For example, an antibody of the invention may be identified as follows. A nucleic acid sequence encoding an antibody, or a fragment thereof, may be inserted into filamentous bacteriophage to generate libraries of approximately $10^7$ or more antibodies. Each phage expresses an antibody on its surface that is encoded by the nucleic acid it contains. Antibodies of the invention may thus be screened and detected by functional and histochemical assays as described herein, and such genes may be subsequently selected and expressed in *E. coli*. This system is described, for example, in U.S. Pat. No. 5,876,691.

Antibodies, or functional fragments thereof, may also be generated using, for example, direct synthesis using recombinant methods. These methods are standard in the art. For example, a nucleic acid sequence may be amplified using the polymerase chain reaction (PCR). The PCR technique is known in the art and is described, for example in U.S. Pat. No. 4,683,195. Using standard methods, and as described herein, the sequence of a monoclonal antibody expressed by a hybridoma may be obtained and functional fragments of the antibody may be amplified. For example, whole RNA may be isolated from a hybridoma expressing a tumor-specific monoclonal antibody. cDNA may then be generated from the RNA using reverse transcriptase and the cDNAs which contain the functional fragments of the variable regions of the heavy and light chains may be amplified using PCR. The PCR products may then be purified and cloned into expression vectors, e.g., plasmid or viral vectors. Many standard vectors are available and the selection of the appropriate vector will depend on, for example, the size of the DNA inserted into the vector and the host cell to be transfected with the vector.

The nucleic acid molecules of the invention may be expressed in a variety of standard vectors and host cells. Any promoter that is active in the host cell may be used to express a nucleic acid molecule. Nonetheless, for expression of an antibody or a fragment of an antibody in a mammalian cell, use of an immunoglobulin gene promoter is desirable. Methods of introducing a vector into a host cell are standard in the art and include, electroporation, use of synthetic lipid polymers, e.g., Lipofectin™, use of calcium chloride, and use of DEAE Dextran. Such methods are also described in, for example, Ausubel et al., *Current Protocols in Molecular Biology*, Wiley Interscience, New York, 2001; and Sambrook et al., *Molecular Cloning: A Laboratory Manual*, Cold Spring Harbor Laboratory, N.Y., 1989.

Isolation of Amino Acid Variants of a Polypeptide

Amino acid sequence variants of a polypeptide, such as an antibody, e.g., a PM-1, PM-2, or CM-2 antibody, can be prepared by introducing appropriate nucleotide changes into the DNA encoding the antibody, or by in vitro synthesis of the desired polypeptide. Such variants include, for example, deletions from, or insertions or substitutions of, residues within the amino acid sequence of the PM-1, PM-2, or CM-2 antibody. Any combination of deletion, insertion, and substitution can be made to arrive at the final construct, provided that the final construct possesses the desired characteristics, e.g., the ability to induce apoptosis of a neoplastic cell, but not a non-neoplastic cell, or the ability to inhibit the proliferation of a neoplastic cell, but not a non-neoplastic cell. The amino acid changes also may alter post-translational processes of an antibody, such as changing the number or position of glycosylation sites, altering the membrane anchoring characteristics, or modifying its susceptibility to proteolytic cleavage.

In designing amino acid sequence variants of a polypeptide, such as an antibody, the location of the mutation site and the nature of the mutation will depend on characteristic(s) to be modified. The sites for mutation can be modified individually or in series, e.g., by substituting first with conservative amino acid choices and then with more radical selections depending upon the results achieved, or deleting the target residue.

A useful method for identification of specific residues or regions for mutagenesis in a polypeptide is called "alanine scanning mutagenesis" and is described, for example, by Cunningham and Wells (Science 244:1081-1085, 1989). Here, a residue or group of target residues are identified (e.g., charged residues such as arg, asp, his, lys, and glu) and replaced by a neutral or negatively charged amino acid (most desirably alanine or polyalanine) to affect the interaction of the amino acids with the surrounding aqueous environment in or outside the cell. The domains demonstrating functional sensitivity to the substitutions then are refined by introducing further or other variants at or for the sites of substitution. Thus, while the site for introducing an amino acid sequence variation is predetermined, the nature of the mutation need not be predetermined. For instance, to optimize the performance of a mutation at a given site, alanine scanning or random mutagenesis may be conducted at the target codon or region and the expressed variants are screened for, e.g., the ability to induce apoptosis of a neoplastic cell and not a non-neoplastic cell, or to inhibit the proliferation of a neoplastic cell and not a non-neoplastic cell.

The sites of greatest interest for substitutional mutagenesis include sites identified as affecting the biological activity of a polypeptide. These sites, especially those falling within a sequence of at least three other identically conserved sites, may be substituted in a relatively conservative manner. For instance, ala may be substituted with val, leu, or ile; arg may be substituted with lys, gln, or asn; asn may be substituted with gln, his, lys, or arg; asp may be substituted with glu; cys may be substituted with ser; gln may be substituted with asn; glu may be substituted with asp; gly may be substituted with pro; his may be substituted with asn, gln, lys, or arg; ile may be substituted with leu, val, met, ala, or phe; leu may be substituted with ile, val, met, ala, or phe; lys may be substituted with arg, gin, or asn; met may be substituted with leu, phe, or ile; phe may be substituted with leu, val, ile, or ala; pro may be substituted with gly; ser may be substituted with thr; thr may be substituted with ser; trp may be substituted with tyr; tyr may be substituted with trp, phe, thr, or ser; and val may be substituted with ile, leu, met, or phe.

Conjugation of the Antibody with a Detectable Agent

If desired, the claimed polypeptide such as an antibody (e.g., monoclonal antibody, such as PM-1, PM-2, or CM-2), or a fragment thereof, may be linked to a detectable agent to facilitate the purification of the polypeptide as well as the diagnosis, monitoring, or treatment of cancer in a mammal in need thereof. The selection of suitable detectable agent will depend on the intended use of the polypeptide and will be apparent to those of ordinary skill in the art. Detectable agents according to the claimed invention include, for example, protein purification tags, cytotoxins, enzymes, paramagnetic labels, enzyme substrates, co-factors, enzyme inhibitors, dyes, radionuclides, chemiluminescent labels, fluorescent markers, growth inhibitors, and biotin.

A protein purification tag may be conjugated to the polypeptide of the invention, to facilitate isolation of the polypeptide. Examples of tags that can be used include His-tags, HA-tags, FLAG®-tags, and c-Myc tags. An enzymatic or chemical cleavage site may be engineered between the polypeptide and the tag moiety so that the tag can be removed following purification. Suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Examples of suitable radioisotopic labels include $^3$H, $^{125}$I, $^{131}$I, $^{32}$P, $^{35}$S, and $^{14}$C. Desirably, the radioisotope will emit in the 10-5,000 kev range, more desirably 100-500 kev. Paramagnetic isotopes may also be conjugated to the polypeptide and used in vivo for the diagnosis and treatment of cancer. The use of such conjugated antibodies may be for in vivo nuclear magnetic resonance imaging. Such a method has previously been described (see, for example, Schaefer et al., JACC 14:472-480, 1989; Shreve et al., Magn. Reson. Med. 3:336-340, 1986; Wolf, Physiol. Chem. Phys. Med. NMR 16:93-95, 1984; Wesbey et al., Physiol. Chem. Phys. Med. NMR 16:145-155, 1984; and Runge et al., Invest. Radiol. 19:408-415, 1984). Alternatively, the radiolabeled antibody may also be used in radioimmunoguided surgery (RIGS), which involves the surgical removal of any tissue the labeled antibody binds to. Thus, the labeled antibody guides the surgeon towards neoplastic tissue by distinguishing it from non-neoplastic tissue. Radiolabels useful for tumor imaging are preferably short-lived radioisotopes. Various radioactive metals with half-lives ranging from 1 hour to 11.4 days are available for conjugation to antibodies, such as scandium-47 (3.4 days), gallium-67 (2.8 days), gallium-68 (68 minutes), technetium-99m (6 hours), indium-111 (3.2 days), and radium-223 (11.4 days), of which gallium-67, technetium-99m, and indium-111 are preferable for gamma camera imaging, gallium-68 is preferable for positron emission tomography, and scandium-47 and radium-223 (and other alpha-emitting radionuclides) are preferable for tumor therapy.

Examples of suitable fluorescent markers include fluorescein, isothiocyalate, rhodamine, phycoerythrin, phycocyanin, allophycocyanin, ophthaldehyde, and fluorescamine. Examples of chemiluminescent markers include a luminal label, isoluminal label, aromatic acridinium ester label, imidazole label, acridinium salt label, oxalate ester label, luciferin label, luciferase label, and aequorin label. Those of ordinary skill in the art would know of other suitable labels, which may be employed in accordance with the present invention. Conjugation of these detectable agents to the claimed polypeptides such as monoclonal antibodies, or fragments thereof, can be accomplished using standard techniques commonly known in the art. Typical antibody conjugation techniques are described by Kennedy et al. (*Clin. Chim. Acta* 70, 1-31, 1976) and Schurs et al. (*Clin. Chim. Acta* 81, 1-40, 1977) and include, for example, the glutaraldehyde method, the periodate method, the dimaleimide method, the m-maleimidobenzyl-N-hydroxy-succinimide ester method. Antibodies may be radiolabeled by any of several techniques known to the art, described, for example, in U.S. Pat. No. 4,444,744. All of these methods are incorporated by reference herein.

In all aspects of the present invention, it is understood that mixtures of different or the same labeled polypeptides specific to different antigens or different epitopes of the same antigen associated with the same or different tumor or tumor cell types may be used. Such a combination may enhance detection, localization and/or therapy in certain cases, and can also increase the range of a broad screen for more than one neoplasm or type of neoplasm.

Polypeptides Conjugated to Anti-Tumor Agents

Although the polypeptide of the invention may induce apoptosis of neoplastic cells, inhibit cellular proliferation of neoplastic cells, or both, the polypeptide may in addition be conjugated to an agent that kills neoplastic cells or that inhibits their proliferation. The targeting ability of the polypeptide, such as an antibody or fragment thereof, results in the delivery to deliver of the cytotoxic or anti-proliferative agent to the tumor to enhance the destruction of the tumor. The polypeptide therefore may be used for the treatment and prevention of cancer in a mammal, such as a human patient. The cytotoxic agent linked to the polypeptide may be any agent that destroys or damages a tumor cell or tumor to which the polypeptide has bound. Examples of such agents include chemotherapeutic agents or radioisotopes, enzymes which activates a pro-drug, or a cytokine.

Suitable chemotherapeutic agents are known to those skilled in the art and include, for example, taxol, mithramycin, deoxyco-formycin, mitomycin-C, L-asparaginase, interferons (especially IFN-alpha), etoposide, teniposide, anthracyclines (e.g., daunomycin and doxorubicin), methotrexate, vindesine, neocarzinostatin, cis-platinum, chlorambucil, cytosine arabinoside, 5-fluorouridine, melphalan, ricin, and calicheamicin. The chemotherapeutic agents may be conjugated to the antibody using conventional methods known in the art.

Suitable radioisotopes for use as cytotoxic agents are also known to those skilled in the art and include, for example, $^{131}$I, or an astatine such as $^{211}$At. These isotopes may be attached to the polypeptide, either covalently or non-covalently, using conventional techniques known in the art.

Alternatively, the cytotoxic agent may also be an enzyme, which activates a pro-drug. This allows the conversion of an inactive pro-drug to its active, cytotoxic form at the tumor site and is called "antibody-directed enzyme pro-drug therapy" (ADEPT). Thus, the polypeptide-enzyme conjugate may be administered to the patient and allowed to localize in the region of the tumor to be treated. The pro-drug is then administered to the patient such that conversion to the cytotoxic drug is localized in the region of the tumor to be treated under the influence of the localized enzyme. An exemplary enzyme is bacterial carboxypeptidase G2 (CPG2) the use of which is described in, for example, WO 88/07378. The polypeptide-enzyme conjugate may, if desired, be modified in accordance with the teaching of WO 89/00427, such as to accelerate its clearance from areas of the body that are not in the vicinity of a neoplasm. The polypeptide-enzyme conjugate may also be used in accordance with WO 89/00427, for example, by providing an additional component, which inactivates the enzyme in areas of the body that are not in the vicinity of the tumor.

As another alternative, the cytotoxic agent conjugated to the claimed polypeptide may also be a cytokine such as interleukin-2 (IL-2), interleukin-4 (IL-4), or tumor necrosis factor alpha (TNF-alpha). The polypeptide targets the cytokine to the tumor so that the cytokine mediates damage to or destruction of the tumor without affecting other tissues. The cytokine may be fused to the polypeptide at the DNA level using conventional recombinant DNA techniques.

In addition, any inhibitor of cell proliferation. e.g., genistein, tamoxifen, or cyclophosphamide, may be conjugated with a polypeptide of the invention.

Dosage

With respect to the therapeutic methods of the invention, it is not intended that the administration of the claimed polypeptide to a patient be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to decrease the number of neoplastic cells by inducing apoptosis of neoplastic cells, by inhibiting proliferation of tumor cells, or both. The compound(s) may be administered to the patient in a single dose or in multiple doses. When multiple doses are administered, the doses may be separated from one another by, for example, one day, two days, one week, two weeks, or one month. For example, the polypeptide (e.g., a monoclonal antibody, such as PM-1, PM-2, or CM-2) may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. The precise dose will vary dependent on the polypeptide used, the density, on the tumor surface, of the ligand to which the polypeptide binds, and the rate of clearance of the polypeptide. For example, the dosage of the PM-1, PM-2, or CM-2 antibody can be increased if the lower dose does not provide sufficient anti-neoplastic activity. Conversely, the dosage of the PM-1, PM-2, or CM-2 antibody can be decreased if the neoplasm is cleared from the patient.

While the attending physician ultimately will decide the appropriate amount and dosage regimen, a therapeutically effective amount of the claimed polypeptide, such as a monoclonal antibody or a fragment thereof, may be, for example, in the range of about 0.1 mg to 50 mg/kg body weight/day or 0.70 mg to 350 mg/kg body weight/week. Desirably a therapeutically effective amount is in the range of about 0.50 mg to 20.0 mg/kg, and more desirably in the range of about 0.50 mg to 15.0 mg/kg for example, about 0.2, 0.3, 0.5, 1.0, 1.5, 2.0, 2.5, 3.0, 3.5, 4.0, 4.5, 5.0, 5.5, 6.0, 7.0, 8.0, 8.5, 9.0, 10.0, 11.0, 12.0, 13.0, 14.0, or 15.0 mg/kg body weight administered daily, every other day, or twice a week.

For example, a suitable dose is an amount of the polypeptide that, when administered as described above, is capable of inducing apoptosis, and is at least 20% above the basal (i.e., untreated) level. In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. According to this invention, the administration of the polypeptide can induce neoplastic cell apoptosis by at least 20%, 40%, 50%, or 75% above that of an untreated control as measured by any standard assay known in the art. More desirably, apoptosis is induced by 80%, 90%, 95%, or even 100% above that of an untreated control. Alternatively, the administration of the polypeptide can inhibit neoplastic cell proliferation by at least 20%, 40%, 50%, or 75% below that of an untreated control as measured by any standard assay known in the art. More desirably, proliferation is inhibited by 80%, 90%, 95%, or even 100% below that of an untreated control. Most desirably, the polypeptide can simultaneously inhibit proliferation and induce apoptosis of neoplastic cells relative to untreated control cells. Such responses can be monitored by any standard technique known in the art. In general, for pharmaceutical compositions, the amount of antibody present in a dose ranges from about 25 µg to 5 mg per kg of host. Suitable dose sizes will vary with the size of the patient, but will typically range from about 0.1 mL to about 5 mL.

Formulation of Pharmaceutical Compositions

The claimed polypeptide may be administered by any suitable means that results in a concentration having anti-neoplastic properties upon reaching the target region. The polypeptide may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. If the neoplastic cells are in direct contact with the blood (e.g., leukemias), or if the tumor is only accessible by the bloodstream then the intravenous (I.V.) route may be used. In cases in which tumors grow in confined spaces such as the pleural cavity or the peritoneal cavity, the polypeptide may be directly administered into the cavity rather than into the blood stream. The formulation and preparation of such compositions are well known to those skilled in the art of pharmaceutical formulation. Formulations can be found in Remington: The Science and Practice of Pharmacy, supra.

Diagnosis and Monitoring Cancer Progression

As discussed above, the present invention is directed to a method for detecting or diagnosing a neoplasm in a mammal, preferably a human patient. Typically, any neoplasm in which administration of the claimed polypeptide causes an induction in apoptosis or a reduction in proliferation are amenable to the methods of this invention.

The claimed polypeptides are particularly useful since they are specific to neoplasms or neoplastic cells, but not normal cells or tissue. Accordingly, this polypeptide can bind to neoplastic cells within the tumor, but not the normal surrounding tissue, thus allowing the detection, the treatment, or both, of a neoplasm in a mammal. For instance, one may use a polypeptide of the invention to determine is a biopsy removed the entire tumor by verifying that no cells bound by the polypeptide remain in the patient or, by verifying that tumor removed from the patient is entirely surrounded by cells that are not bound by the polypeptide.

It is understood that to improve the sensitivity of detection, multiple neoplastic markers may be assayed within a given sample or individual. Thus, polypeptides such as antibodies or functional fragments specific for different antigens may be combined within a single assay, or in multiple assays. Further, multiple primers or probes specific to neoplasms may be used concurrently. The selection of markers may be based on routine experiments to determine combinations that results in optimal sensitivity.

In Vitro Detection of a Neoplasm

In general, the diagnosis of a neoplasm in a mammal involves obtaining a biological sample from the mammal (e.g., human patient), contacting such sample with the polypeptide of the invention (e.g., a monoclonal antibody, such as PM-1, PM-2, or CM-2), detecting in the sample the level of reactivity or binding of the polypeptide to neoplastic cells relative to a control sample, which corresponds to non-neoplastic cells derived from healthy tissue from the mammal in which the cancer is being diagnosed or from another patient known not to have neoplasm. Thus, the methods of this invention are particularly useful for the detection of early stage tumors or metastases, which are otherwise undetectable. Accordingly, in addition to diagnosing a neoplasm in a patient, the methods of this invention may also be used to monitor progression of a neoplasm in a mammal. The polypeptides described herein therefore may be used as markers for the progression of a neoplasm. For this purpose, the assays described below, which are used for the diagnosis of a neoplasm, may be performed over time, and the change in the level of reactive polypeptide(s) evaluated. For example, the assays may be performed every 24-72 hours for a period of 6 months to 1 year, and thereafter performed as needed. In general, a neoplasm is progressing in those patients in whom the level of bound polypeptide detected increases over time. In contrast, the neoplasm is not progressing when the level of bound polypeptide either remains constant or decreases with time. Alternatively, as is noted above, the polypeptide of the invention may also be used to determine the presence of tumor cells in the mammal following tumor resection by surgical intervention to determine whether the tumor has been completely removed from the mammal.

Desirably, the polypeptide is linked to a detectable agent, which facilitates detection, or measurement of polypeptide reactivity. The biological sample is any biological material, which may contain neoplastic cells and include, for example, blood, saliva, tissue, serum, mucus, sputum, urine, or tears. The biological sample may also be a tissue section, which may be fixed tissue, fresh tissue, or frozen tissues. A neoplasm is detected or diagnosed in the mammal from which the sample was obtained if there is an increase in the level of reactivity of the antibody with the biological sample over the control sample. Such increase is at least 10%, 20%, 30%, 40%, 50%, or more than 50% over control levels. The level of binding or reactivity can be determined by any method known in the art and is described in further detail below.

In Vitro Diagnostic Assays

The diagnosis of neoplasms using the claimed polypeptide may be performed by any method known to those of ordinary skill in the art for using a binding agent to detect polypeptide markers in a sample. See, e.g., Harlow and Lane, Antibodies: A Laboratory Manual, Cold Spring Harbor Laboratory, 1988. For example, the polypeptide may be used for enzyme-linked immunosorbent assay (ELISA), Western blotting or in situ detection of tumor cells in a tissue sample. For example, the ELISA assay typically involves the use of the polypeptide, such as an antibody, immobilized on a solid support to bind to the tumor cells in the biological sample. The bound tumor cell may then be detected using a detection reagent that contains a reporter group and that specifically binds to the antibody/tumor cell complex. Such detection reagents include, for example, any binding agent that specifically binds to the antibody, such as an anti-immunoglobulin, protein G, protein A, or a lectin. Alternatively, a competitive assay may be utilized, in which the polypeptide is an antibody and in which the antigens, to which the antibody is specific to is labeled with a reporter group and allowed to bind to the immobilized antibody after incubation of the antibody with the biological sample. The extent to which components of the sample inhibit the binding of the labeled antigens to the antibody is indicative of the reactivity of the sample with the immobilized antibody. Diagnosis of a neoplasm in a patient may also be determined by a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group. For example, to determine the presence or absence of a neoplasm, such as colorectal adenocarcinoma, the signal detected from the reporter group that remains bound to the solid support is generally compared to a signal that corresponds to a predetermined cut-off value. The cut-off value for the detection of a neoplasm is the average mean signal obtained when the antibody is incubated with samples from patients without a neoplasm.

The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

The polypeptides of the invention may also be employed histologically for in situ detection or quantitative determination of tumor cells, for example, by immunofluorescence or immunoelectron microscopy. In situ detection or determination may be accomplished by removing a tissue specimen from a patient and allowing a labeled antibody to bind to any tumor cell in the specimen. Using such a procedure not only allows the detection of neoplastic cells in a sample, but also allows for the determination of their spatial distribution. As another example, the biological sample can be a smear of biological material containing neoplastic cells on a slide, and the detection of neoplastic cells in the biological material is achieved by examining the smear with a microscope or by fluocytometry.

In Vivo Detection of a Neoplasm

Alternatively, the antibody of the invention may also be used in vivo for detecting and localizing a neoplasm. Such a method may involve injecting a mammal, desirably a human subject, parenterally with a polypeptide of the invention, such as PM-1, PM-2, or CM-2, which has been labeled with a detectable agent, and is described, for instance, in U.S. Pat. No. 4,444,744. For example, the polypeptide can be radiolabeled with a pharmacologically inert radioisotope and administered to the patient. The activity of the radioisotope can be detected in the mammal using a photoscanning device, and an increase in activity relative to a control reflects the detection and localization of a neoplasm.

Treatment

In addition to the diagnosis and monitoring of neoplasms in mammals, the present invention also features methods for treating neoplasms in a mammal, desirably a human patient. The method generally involves the administration of a biologically effective amount of the polypeptide of the invention to the patient. The polypeptide is typically administered to the mammal by means of injection using any routes of administration such as by intrathecal, subcutaneous, submucosal, or intracavitary injection as well as for intravenous or intraarterial injection. Thus, the polypeptide may be injected systemically, for example, by the intravenous injection of the polypeptide such as the PM-1, PM-2, or CM-2 antibody into the patient's bloodstream or alternatively, the polypeptide can be directly injected at the site of the neoplasm or at a location in proximity to the neoplastic cells.

In general, and as discussed above, binding of the polypeptide of the invention to neoplastic cells results in an induction in apoptosis, a reduction in cellular proliferation, or both relative to the control sample. Alternatively, the antibodies may also activate the complement pathway, which ultimately causes holes to be punctured into the cellular membrane, resulting in cell death.

If desired, the polypeptides may also be conjugated to drugs or toxins as described above. Once attached to the cell surface, the conjugate may be engulfed into the cell cytoplasm where cell enzymes cleave, and, thus, activate or free the drugs or toxins from the conjugate. Once released, the drugs or toxins damage the cell and irreversibly induce cell death. With respect to radiolabeled antibodies, binding to neoplastic cells and the resulting emission of radiation, at a short distance from the cell DNA, produces damage to the latter thus inducing cell death in the next replication round. For example, after a neoplasm has been detected and localized in a subject, a higher dose of labeled antibody, generally from 25 to 250 mCi for $^{131}$I, and preferably from 50 nCi to 150 mCi per dose, based on a 70 kg patient weight, is injected. Injection may be intravenous, intraarterial, intralymphatic, intrathecal, or intracavitary, and may be repeated more than once. It may be advantageous for some therapies to administer multiple, divided doses of radiolabeled polypeptides or polypeptide mixtures, e.g., in the range of 20-120 mCi (70 kg patient), thus providing higher cell-killing doses to the neoplasm without usually effecting a proportional increase in radiation of normal tissues Therapy using labeled polypeptides is advantageously used as a primary therapeutic treatment, but may also be used in combination with other anti-neoplastic therapies, e.g., radiation and chemotherapy, and as an adjunct to surgery. The administration of such conjugated polypeptides is particularly useful in the case where small metastases cannot be surgically removed.

Combination of a Polypeptide with Other Anti-Neoplastic Therapies

Chemotherapeutic agents and/or radiation and/or surgical removal of the neoplasm can optionally be combined with any of the methods of the present invention. Classes of compounds that can be used as the chemotherapeutic agent include: alkylating agents, antimetabolites, natural products and their derivatives, hormones and steroids (including synthetic analogs), and synthetics. Examples of alkylating agents (e.g., nitrogen mustards, ethylenimine derivatives, alkyl sulfonates, nitrosoureas and triazenes) include Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide. Antimetabolites (including folic acid antagonists, pyrimidine analogs, purine analogs and adenosine deaminase inhibitors) may include, for example, Methotrexate, 5-Fluorouracil, Floxuridine, Cytarabine, 6-Mercaptopurine, 6-Thioguanine, Fludarabine phosphate, Pentostatine, and Gemcitabine. Natural products and their derivatives (including vinca alkaloids, antitumor antibiotics, enzymes, lymphokines and epipodophyllotoxins) may also be used and include, for example, Vinblastine, Vincristine, Vindesine, Bleomycin, Dactinomycin, Daunorubicin, Doxorubicin, Epirubicin, Idarubicin, paclitaxel (paclitaxel is commercially available as Taxol, Mithramycin, Deoxyco-formycin, Mitomycin-C, L-Asparaginase, Interferons (especially IFN-alpha), Etoposide, and Teniposide. Hormones and steroids (including synthetic analogs) include, for example, 17-alpha-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, or Zoladex. Exemplary synthetics (including inorganic complexes such as platinum coordination complexes) include Cisplatin, Carboplatin, Hydroxyurea, Amsacrine, Procarbazine, Mitotane, Mitoxantrone, Levamisole, and Hexamethylmelamine.

Methods and dosages for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the disclosure of which is incorporated herein by reference.

The following examples are provided for the purpose of illustrating the invention and should not be construed as limiting.

EXAMPLE 1

Materials and Methods

Cell Culture

In this study the following human cell lines were used: BXPC-3 (pancreatic adenocarcinoma; ATCC (American Type Culture Collection, P.O. Box 1549, Manassas, Va. 20108) Accession No. CRL-1687), CACO-2 (colon adenocarcinoma), Colo-206F (colon carcinoma). The cell lines were cultured in RPM1-1640 media (PAA, Vienna, Austria) supplemented with 10% fetal calf serum (FCS), 2 mM glutamine and penicillin/streptomycin (both 1%) and incubated in a humidified, 5% $CO_2$ atmosphere at 37° C. For the assays described, cells were grown to sub-confluency, detached with trypsin/EDTA and washed twice with phosphate-buffered saline (PBS) before use.

Producing Hybridomas

We immortalized lymphocytes by fusing them to the HAB-1 heteromyeloma as follows.

We washed the HAB-1 heteromyeloma cells twice with RPMI 1640 (PAA, Vienna, Austria) without additives and centrifuged the cells for 5 minutes at 1500 rpm. We then thawed frozen lymphocytes obtained from either the spleen or the lymph nodes and we washed these cells twice with RPMI 1640 without additives and centrifuged these cells at 1500 rpm for 5 minutes. Both the HAB-1 and the lymphocyte cell pellets were resuspended in 10 ml RPMI 1640 without additives and were counted in a Neubauer cell counting chamber. We washed the cells again, added the HAB-1 cells and the lymphocytes together in a ratio of 1:2 to 1:3, mixed them, and centrifuged the mixture for 8 minutes at 1500 rpm. We pre-warmed Polyethylene Glycol 1500 (PEG) to 37° C. and carefully let the PEG run drop-wise onto the pellet while slightly rotating the 50 ml tube. Next, we gently resuspended the pellet and rotated the tube for exactly 90 seconds in a 37° C. water bath. We washed the cells twice with a full 10 ml pipette of RPMI without additives and centrifuged the cells for 5 minutes at 1500 rpm. We added 1 ml of RPMI 1640 with HAT supplement (PAA, Vienna, Austria) and 10% FCS, 1% glutamine, and 1% penicillin/streptomycin ("RPMI 1640 HAT") into each well of a 24-well plate.

The cell pellet was dissolved in RPMI 1640 HAT and 0.5 ml of the cells was added to each well of the 24-well plate. We then placed the 24-well plates into a 37° C. incubator and changed the RPMI 1640 HAT medium weekly. After four to six weeks, the cell culture supernatants were screened for antibody production in an enzyme-linked immunosorbent assay (ELISA).

Using this protocol, approximately 80% to 90% of the triomas generated are viable and approximately 50% secrete immunoglobulins. Positive clones were tested immunohistochemically on autologous tumor tissue sections and clones that showed a positive reaction were subsequently re-cloned.

cDNA Synthesis and RT-PCR

To obtain the sequence of the antibody, we isolated whole RNA from the trioma using the RNASE Kit from Qiagen. Total RNA may also be prepared using methods standard in the art, e.g., those described in Krenn et al. (Clin. Exp. Immunol. 115:168-175, 1999). cDNA synthesis from total RNA obtained from hybridoma cell lines PM-1, PM-2, and CM-2 was performed with 5 µg total RNA using Gibco BRL (Eggenstein, Germany) M-MLV Reverse Transcriptase according to the manufacturer's instructions. The amplification of $V_H$ and $V_L$ genes was carried out in a 25 µl volume with 1.75 mM $MgCl_2$, 0.4 pM primer, 200 µM of each dNTP, and 1 U Taq polymerase (MBI Fermentas, St. Leon-Rot, Germany). The PCR-products were amplified using the following cycle profiles: 95° C. for 2 min, followed by 35 cycles of 94° C. for 30 sec; 65° C. for 30 sec (for VH3 and VH4 primers), 60° C. for VH1, VH2, VH5, VH6 and 52° C. for VL primers respectively; a final extension at 72° C. for 4 min.

Sequencing the Antibody

The PCR products were purified using gel electrophoresis through 2% agarose (Roth, Karlsruhe, Germany) followed by gel extraction of the PCR product using a Jetsorb gel extraction kit (Genomed, Bad Oeynhausen, Germany). The PCR products were then cloned using the pCR-Script Amp $SK^+$ cloning kit (Stratagene, Heidelberg, Germany). Ten positive clones were sequenced using the DyeDeoxy termination cycle sequencing kit (Applied BioSystems Inc., Weiterstadt, Germany) and analysed with an ABIPrism373 automated DNA sequencer (both strands were sequenced using T3 and T7 primers). The sequences were analysed using the DNASIS for Windows sequence comparison software and the GenBank and IMGT/V-QUEST databases. The International Immunogenetics ("IMGT") database is coordinated by Marie-Paule Lefranc at the Université Montpellier, Montpellier, France.

Immunohistochemical Staining of Paraffin Sections

Paraffin-embedded human tissues were sectioned (2 µm), the paraffin was removed as follows:
 Two xylene washes for 5 minutes each,
 Two 100% ethanol washes for 5 minutes each,
 Two 90% ethanol washes for 5 minutes each,
 Two 70% ethanol washes for 5 minutes each, and
 Three washes in distilled $H_2O$.

The slides containing the tissue sections were incubated in 75 ml distilled $H_2O$ and 25 ml de-masking solution (Demaskierungslösung G, Biologo, Kronshagen, Germany) in a preheated water-bath at 100° C. for 20 minutes. The slides were placed into Tris/NaCl (3 grams Tris, 40.5 grams NaCl in 5 liters of distilled $H_2O$ and pH adjusted to 7.4 with HCl) for 5 minutes, blocked for 15-30 minutes with 150 µl of 0.5% Bovine Serum Albumin Fraction V ("BSA;" Roth, Karlsruhe, Germany) in phosphate buffered saline ("PBS") per slide, and washed once with Tris/NaCl.

The sections were incubated with PM-1, PM-2, and CM-2 antibodies, and unrelated, human monoclonal IgM antibodies (ChromPure IgM, Dianova, Hamburg, Germany, 10 µg/ml) or mouse CAM 5.2 antibody diluted 1:50 with BSA/PBS (Dako, Hamburg, Germany) for 2.5 hours in a humidified incubator at 37° C. The sections were then washed three times with Tris/NaCl (3 grams Tris, 40.5 grams NaCl in 5 liters of distilled $H_2O$ and pH adjusted to 7.4 with HCl), followed by incubation with peroxidase-labeled rabbit anti-human or rabbit anti-mouse conjugate (Dako) diluted 1:50 in PBS containing 30% rabbit serum (for antibody 103/51) at RT for 1 hour. After washing three times with Tris/NaCl the tissue sections were incubated in PBS for 10 minutes before staining with diaminobenzidine (0.05%)-hydrogen peroxide (0.02%) for 10 minutes at room temperature (RT). The reaction was stopped using running tap water and the sections counter-stained with hematoxylin. After mounting with glycerol-gelatin, the sections were analyzed using light microscopy.

Immunohistochemical Staining of Cryo-Sections from Autologous Tumors

Frozen human tissues were sectioned (4 µm), fixed in acetone, air-dried and washed with Tris/NaCl (3 grams Tris, 40.5 grams NaCl in 5 liters of distilled $H_2O$ and pH adjusted to 7.4 with HCl). The cryo-sections were then blocked with PBS containing 3% milk powder for 30 minutes at RT. After washing three times with Tris/NaCl the sections were incubated with PM-1, PM-2, or CM-2 human IgM antibodies, unrelated human monoclonal IgM (Chrompure IgM, Dianova, 10 µg/ml) or mouse CAM 5.2 antibody diluted 1:50 with BSA/PBS (Dako) for 30 minutes at RT. The sections were washed three times with Tris/NaCl, followed by incubation with secondary antibodies (peroxidase-labeled rabbit anti-human or rabbit anti-mouse conjugate 1:50) for 30 minutes at RT. After washing three times with Tris/NaCl and incubation in PBS for 10 minutes, the sections were stained with diaminobenzidine (0.05%)-hydrogen peroxide (0.02%) for 10 minutes at RT. The reaction was stopped under running tap water and the sections counterstained with hematoxylin. After mounting with glycerol-gelatin, the sections were analyzed using light microscopy.

Preparation of Tumor Cell Membrane Extracts

Isolation of membrane proteins from tumor cells was performed as described using standard methods in the art, as described, for example, in Hensel et al. (Int. J. Cancer 81:229-235, 1999). In particular, confluent tumor cells (BXPC-3 for PM-1 and PM-2, CACO-2 for CM-2) were washed twice with PBS, harvested with a cell scraper, centrifuged, and resuspended in hypotonic buffer (20 mM HEPES, 3 mM KCl, 3 mM $MgCl_2$) and incubated for 15 minutes on ice. The cells were then sonicated for 5 minutes and the nuclei were pelleted by centrifugation at 10,000×g for 10 min. The supernatant was centrifuged for 40 minutes at 100,000×g in a swing-out rotor to pellet the membranes. After washing the pellet with hypotonic buffer, the pellet was resuspended in membrane lysis buffer (50 mM HEPES pH 7.4, 0.1 mM EDTA, 10% glycerol, and 1% Triton X-100). Complete protease inhibitor (Boehringer, Mannheim, Germany) also was added to all solutions.

Western Blotting

Western blots were preformed using standard techniques as described, for example, in Hensel et al. (Int. J. Cancer 81:229-235, 1999). In short, blotted nitrocellulose membranes were blocked with PBS containing 3% low fat milk powder, followed by incubation for 1 hour with 20-40 µg of PM-1, PM-2, or CM-2 human IgM antibodies or unrelated human control IgM (ChromPure IgM, Dianova). The secondary antibody (peroxidase-coupled rabbit anti-human IgM antibody 1:1,000, Dianova) was detected with the SUPER-SIGNAL chemiluminescence kit from Pierce (KMF, St. Augustin, Germany).

Cytospin Preparation

The adherent growing cells were detached by adding Trypsin/EDTA (PAA, Vienna, Austria) followed by a 5 minute incubation in an humidified incubator (37° C., 5% $CO_2$) and centrifugation for 5 minutes at 1,500 rpm. The cells then were washed twice with 10 ml of RPMI-1640 cell culture medium (PAA, Vienna, Austria). The cell number was adjusted to a density of $1 \times 10^5$ cells/ml. From this solution, 100 µl were centrifuged onto microscope slides with a cytospin centrifuge (CYTOSPIN 2, Shandon, UK) for 2 minutes at 50 rpm. The resultant cytospins were dried for at least 2 hours and stained as specified below.

Immunoperoxidase Staining of Cytospins and Cryosections

Cytospins were dried for at least two hours at room temperature or cryosections were dried for at least two hours after they were cut. The sections or cytospins were then fixed for 10 minutes in acetone. The fixed cryosections/cytospins were dried for 30 minutes at room temperature, washed three times with Tris-NaCl (3 grams Tris, 40.5 grams NaCl in 5 liters of distilled $H_2O$ and pH adjusted to 7.4 with HCl), and placed into Tris/NaCl for 5 minutes. The cryosections/cytospins were blocked for 15-30 minutes with 3% milk powder in PBS (100 µl per cryosection/cytospin) and washed three times with Tris-NaCl. The cryosections/cytospins were incubated in 100 µl of primary antibody per cryosection/cytospin (e.g., at 20 µg/ml in 0.5% BSA/PBS; CK 8 at 1:50 in BSA/PBS; CAM 5.2 at 1:10 in BSA/PBS; or RPMI 1640 media (PAA, Vienna, Austria) as a negative control) for 30 minutes in a humidified chamber at room temperature. Following the incubation, the cryosections/cytospins were washed three times with Tris-NaCl.

The cryosections/cytospins were then incubated in 100 µl of a solution containing the secondary antibody (70% PBS+ 30% rabbit or human serum+e.g., 1:50 rabbit anti-mouse antibody, peroxidase coupled or 1:50 rabbit anti-human IgM antibody, peroxidase coupled; Dako, Hamburg, Germany) per cryosection/cytospin for 30 minutes in a humidified chamber at room temperature and washed three times with Tris-NaCl and placed into PBS for 10 minutes. The cryosections/cytospins where then incubated for 10 minutes in 100 µl of a solution containing 0.05% diaminobenzidine and 0.02% hydrogen peroxide (Sigma, Taufkirchen (München), Germany). Following the incubation, the cryosections/cytospins were washed with distilled $H_2O$ and placed into a hematoxylin staining solution (Roth, Karlsruhe, Germany) for 5 minutes. The cryosections/cytospins were then rinsed for 15 minutes under running tap water, washed with distilled $H_2O$, and cover with pre-warmed glycerol-gelatin.

The following experiments were carried out using the above materials and methods.

EXAMPLE 2

Generation of the Cell Line Expressing the PM-1, PM-2, or CM-2 Monoclonal Antibody As described above, we obtained the PM-1, PM-2, or CM-2 monoclonal antibody expressing hybridoma by fusing lymphocytes obtained from the spleen or lymph nodes of a cancer patient with the heteromyeloma cell line HAB-1 (Faller, et al., Br. J. Cancer 62:595-598, 1990). The lymphoid sources were not pre-selected in terms of the age or sex of the patient. The resultant cell is a type of hybridoma known as a trioma, as it is the fusion of three cells. Like normal B-lymphocytes, this trioma has to ability to produce antibodies. The specificity of the antibody is determined by the specificity of the original lymphocyte from the patient that was used to generate the trioma.

The hybridoma supernatants were screened for antibody production using an ELISA assay. Following ELISA, antibodies were primarily tested immunohistochemically against their autologous tumor for tumor specific reactivity. Antibodies PM-1 und PM-2 were generated from the lymphocytes of a pancreatic cancer patient and the CM-2 antibody was generated from the lymphocytes of a patient with colon carcinoma.

The amino acid sequence (SEQ ID NO:1) and the nucleic acid sequence (SEQ ID NO:2) of the variable region of the light chain of human monoclonal antibody PM-1 are shown in FIG. 12. As indicated in FIG. 12, Complement Determining Region 1 (CDR1) of the PM-1 variable region light chain spans nucleotides 76-93 which encode amino acids 26-31, CDR2 spans nucleotides 145-153 which encode amino acids 49-51, and CDR3 spans nucleotides 262-285, which encode amino acids 88-95.

The amino acid sequence (SEQ ID NO:3) and the nucleic acid sequence (SEQ ID NO:4) of the variable region of the heavy chain of human monoclonal antibody PM-1 are shown in FIG. 13. As indicated in FIG. 13, CDR1 of the PM-1 variable region heavy chain spans nucleotides 31-54 which encode amino acids 11-18, CDR2 spans nucleotides 106-129 which encode amino acids 36-43, and CDR3 spans nucleotides 244-270 which encode amino acids 82-90.

The amino acid sequence (SEQ ID NO:5) and the nucleic acid sequence (SEQ ID NO:6) of the variable region of the light chain of human monoclonal antibody PM-2 are shown in FIG. 14. As indicated in FIG. 14, CDR1 of the PM-2 variable region light chain spans nucleotides 76-102 which encode amino acids 26-34, CDR2 spans nucleotides 154-174 which encode amino acids 52-58, and CDR3 spans nucleotides 289-309, which encode amino acids 97-103.

The amino acid sequence (SEQ ID NO:7) and the nucleic acid sequence (SEQ ID NO:8) of the variable region of the heavy chain of human monoclonal antibody PM-2 are shown in FIG. 15. As indicated in FIG. 15, CDR1 of the PM-2 variable region heavy chain spans nucleotides 31-54 which encode amino acids 11-18, CDR2 spans nucleotides 106-129 which encode amino acids 36-43, and CDR3 spans nucleotides 244-300, which encode amino acids 82-100.

encode amino acids 16-22, CDR2 spans nucleotides 118-141 which encode amino acids 40-47, and CDR3 spans nucleotides 256-300, which encode amino acids 86-100.

EXAMPLE 3

Immunohistochemical Characterization of an Antibody

To characterize the monoclonal antibody secreted by a hybridoma, we tested the antibody against a panel of normal and tumor tissues using an immunoperoxidase assay as described in the materials and methods. This assay provided us with an overview of which tissues were stained by the antibody and of the distribution of the antigen.

Antibodies that are specific for tumor cells and not for normal tissue were further characterized. First, we tested these antibodies against the same types of tumors from different patients. We then tested these antibodies against tumors of other organs and, finally, against normal tissues. Using these assays, we identified the human PM-1, PM-2, and CM-2 monoclonal antibodies. The tumor reactive antibodies generated and described in this study are of the IgM/λ isotype (see Table 1).

TABLE 1

Origin of Monoclonal IgM Antibodies and Clinical Data of Cancer Patients

| Antibody | Organ | Tumour type | Tumour stage | Tumour grade | Age | Sex | Source of Lymphocytes | Ig Class |
|---|---|---|---|---|---|---|---|---|
| PM-1 | Pancreas | Adenocarcinoma | T1N1 | G2-3 | 47 | M | Spleen | IgM/λ |
| PM-2 | | | | | | | | IgM/λ |
| CM-2 | Colon | Adenocarcinoma | T2N0 | G2 | 78 | M | Spleen | IgM/λ |

The amino acid sequence (SEQ ID NO:9) and the nucleic acid sequence (SEQ ID NO:10) of the variable region of the light chain of human monoclonal antibody CM-2 are shown in FIG. 16. As indicated in FIG. 16, CDR1 of the CM-2 variable region light chain spans nucleotides 76-102 which encode amino acids 26-34, CDR2 spans nucleotides 151-162 which encode amino acids 51-54, and CDR3 spans nucleotides 271-297, which encode amino acids 91-99.

To investigate the genetic origin of these human monoclonal IgM antibodies the $V_H$ and $V_L$ genes were amplified, cloned and sequenced. The sequences were compared with germ-line sequences in the IMGT/V-QUEST database to identify the most homologous germ-line genes and to detect somatic mutations. The results are represented in Table 2. The degree of identity of the nucleotide sequences of the $V_H$ segment to those of the closest reported germ-line $V_H$ genes ranged from 97.2 to 100% as summarized in Table 2.

TABLE 2

Characterization of Variable Heavy and Light Chain Regions of Monoclonal IgM Antibodies

| | Heavy chain | | | | Light chain | | | |
|---|---|---|---|---|---|---|---|---|
| Antibody | Germ-line gene | Homology (%) | R/S Frame | R/S CDR | Germ-line gene | Homology (%) | R/S Frame | R/S CDR |
| PM-1 | IGHV3-23*01 | 100 | 0/0 | 0/0 | IGLV3-10*01 | 99.0 | 2/1 | 0/0 |
| PM-2 | IGHV3-23*01 | 100 | 0/0 | 0/0 | IGLV5-45*01 | 98.2 | 3/2 | 0/0 |
| CM-2 | IGHV5-51*01 | 97.2 | 2/1 | 3/2 | IGLV2-14*01 | 97.2 | 0/2 | 4/2 |

The amino acid sequence (SEQ ID NO:11) and the nucleic acid sequence (SEQ ID NO:12) of the variable region of the heavy chain of human monoclonal antibody CM-2 are shown in FIG. 17. As indicated in FIG. 17, CDR1 of the CM-2 variable region heavy chain spans nucleotides 46-66 which Different VH genes of the VH3, VH4 and VH5 gene family expressed the antibodies. The high homology of the VH regions to the germ-line genes and the low R/S ratio, which is an indicator for affinity maturation of antibodies, indicates that none of the antibodies underwent affinity maturation by somatic mutation due to antigen contact. The degree of identity of the nucleotide sequences of the $V_L$ segment to their most homologous $V_L$ germ-line genes ranged from 97.2 to 99.0%, with all five antibodies utilizing λ-light chain genes. The R/S ratio is again low and with one exception (antibody CM-2) restricted to the framework region. The data indicate that all three antibodies belong to the family of naturally occurring, non-affinity matured antibodies.

After initial testing on autologous tumors, the reaction patterns of the antibodies were investigated in greater detail using immunohistochemical staining on a variety of paraffin- and cryo-embedded carcinomas and normal tissues. The PM-1, PM-2, and CM-2 antibodies exhibited no binding activity with normal tissues (Table 3).

TABLE 3

Reaction Pattern of the Monoclonal IgM Antibodies on Normal Tissues

| Tissue | PM-1 | PM-2 | CM-2 | CAM 5.2 | M6 (IgM-Control) |
|---|---|---|---|---|---|
| Stomach | − | − | − | + | − |
| Colon | − | − | − | + | − |
| Lung | − | − | − | − | − |
| Esophagus | − | − | − | − | − |
| Urinary bladder | − | − | − | − | − |
| Prostate | − | − | − | − | − |
| Breast | − | − | − | − | − |
| Pancreas | − | − | − | − | − |
| Small Intestine | − | − | − | + | − |

In addition, the CM-2 antibody failed to stain the following normal tissues: thyroid, aorta, myocardium, pericardium, tongue, small intestine, corpus pineal, pituitary, bone marrow, blood, cerebellum, rectum, thymus, tonsilla palatina, lymph nodes, adrenal gland, ductus deferens, ovary, tuba uterina, corpus uteri, cervix uteri (portio vag.), skin, skeletal muscle, placenta, spinal marrow, and cerebral cortex. The CM-2 antibody also failed to stain the following fetal tissues: lung, stomach, ileum, pancreas, liver, spleen, thymus, kidney, spinal marrow, cerebral cortex, cerebellum, corpus pineal, and pituitary.

In contrast, the antibodies show a very heterogeneous reactivity pattern with tumor tissues. The PM-2 antibody, for example, reacts with a large number of the carcinomas tested in this study, whereas the reactivity of antibody CM-2 is more restricted (for details see Table 4).

TABLE 4

Reaction Pattern of the Monoclonal IgM Antibodies on Tumor Tissues

| Tissue | Carcinoma type | PM-1 +/− | PM-2 +/− | CM-2 +/− | CAM5.2 | M6 (IgM-Control) |
|---|---|---|---|---|---|---|
| Stomach | Adeno | 3/1 | 3/0 | 0/3 | + | − |
| Colon | Adeno | 2/1 | 3/0 | 11/16 | + | − |
| Small Intestine | | 1/0 | 1/0 | n.d. | + | − |
| Lung | Adeno | 3/1 | 3/0 | 0/4 | + | − |
| | Squamous cell | 2/2 | 3/0 | 0/3 | +(CK5/6) | − |
| Liver | | 1/1 | 2/0 | 0/2 | + | − |
| Esophagus | Squamous cell | 3/0 | 3/0 | 0/3 | +(CK5/6) | − |
| Pancreas | Adeno | 5/1 | 6/0 | 0/6 | + | − |
| Urinary bladder | Urothel | 0/1 | 1/0 | 0/1 | + | − |
| Kidney | Renal cell | 0/1 | 1/0 | 0/1 | − | − |
| | Adeno | n.d. | n.d. | 0/2 | + | − |
| Prostate | Adeno | 1/4 | 4/1 | 0/5 | + | − |

TABLE 4-continued

Reaction Pattern of the Monoclonal IgM Antibodies on Tumor Tissues

| Tissue | Carcinoma type | PM-1 +/− | PM-2 +/− | CM-2 +/− | CAM5.2 | M6 (IgM-Control) |
|---|---|---|---|---|---|---|
| Breast | Invasive (ductal) | 2/1 | 3/0 | 0/3 | + | − |
| | Invasive (lobular) | 2/1 | 3/0 | 0/3 | + | − |
| Ovary | Adeno | 1/1 | 3/0 | 0/2 | + | − |
| Uterus | Adeno | 1/2 | 3/0 | 0/3 | + | − |
| Adrenal Gland | Adeno | 1/0 | 1/0 | n.d. | + | − |

Figure 2:
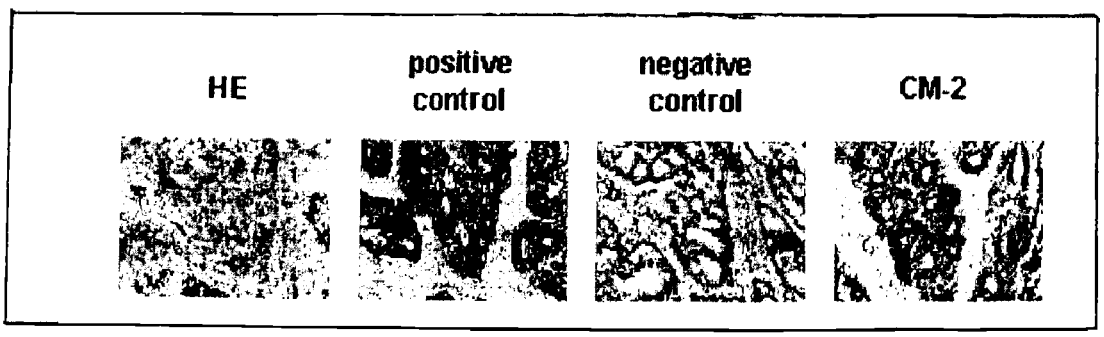
FIG. 2 is a series of images showing immunohistochemical staining of CM-2 of an adenocarcinoma of the colon. Paraffin sections were stained with hematoxylin-eosin, positive control antibody (AE1/AE3 for adenocarcinoma of the colon), secondary antibody alone as a negative control, and antibody CM-2. The original magnification for these images was 200×.

The positive reaction of antibody PM-1 was not restricted to adenocarcinoma of the pancreas as clear positive reactions were observed, among others, on squamous cell carcinoma of the lung (FIGS. 1A and 1B). Antibody PM-2 gave a broad staining pattern on a variety of tumor tissues that were tested (FIGS. 1C and 1D). FIG. 2 shows the reactivity of the CM-2 antibody on a colon carcinoma. As shown in this Figure, the CM-2 antibody stains cancerous colon tissue. The CM-2 antibody also stains adenocarcinomas of the endometrium. In addition to the tissues shown in Table 4, the CM-2 antibody also fails to stain the following tumor tissues: carcinomas of the thryoid, bronchi (squamous cell, small cell, and large cell), hepatocytes, and cholangio cells, as well as nephroblastomas, seminomas, yolk sac tumors, teratomas, teratocarcinomas, melanomas, thymomas, fibrosarcomas, myxofibrosarcomas, rhabdomyoscarcomas, leiomyosacromas, neuroblastomas, squamous cell carcinomas of the oropharynx, and acute myeloid leukemias. The positive control antibody used in these experiments was a mouse monoclonal antibody against human cytokeratin 5/6 ("CK 5/6;" Dako A/S, Denmark) or a mouse monoclonal antibody against human cytokeratin ("CAM 5.2;" Becton Dickinson, New Jersey).

Figure 5:
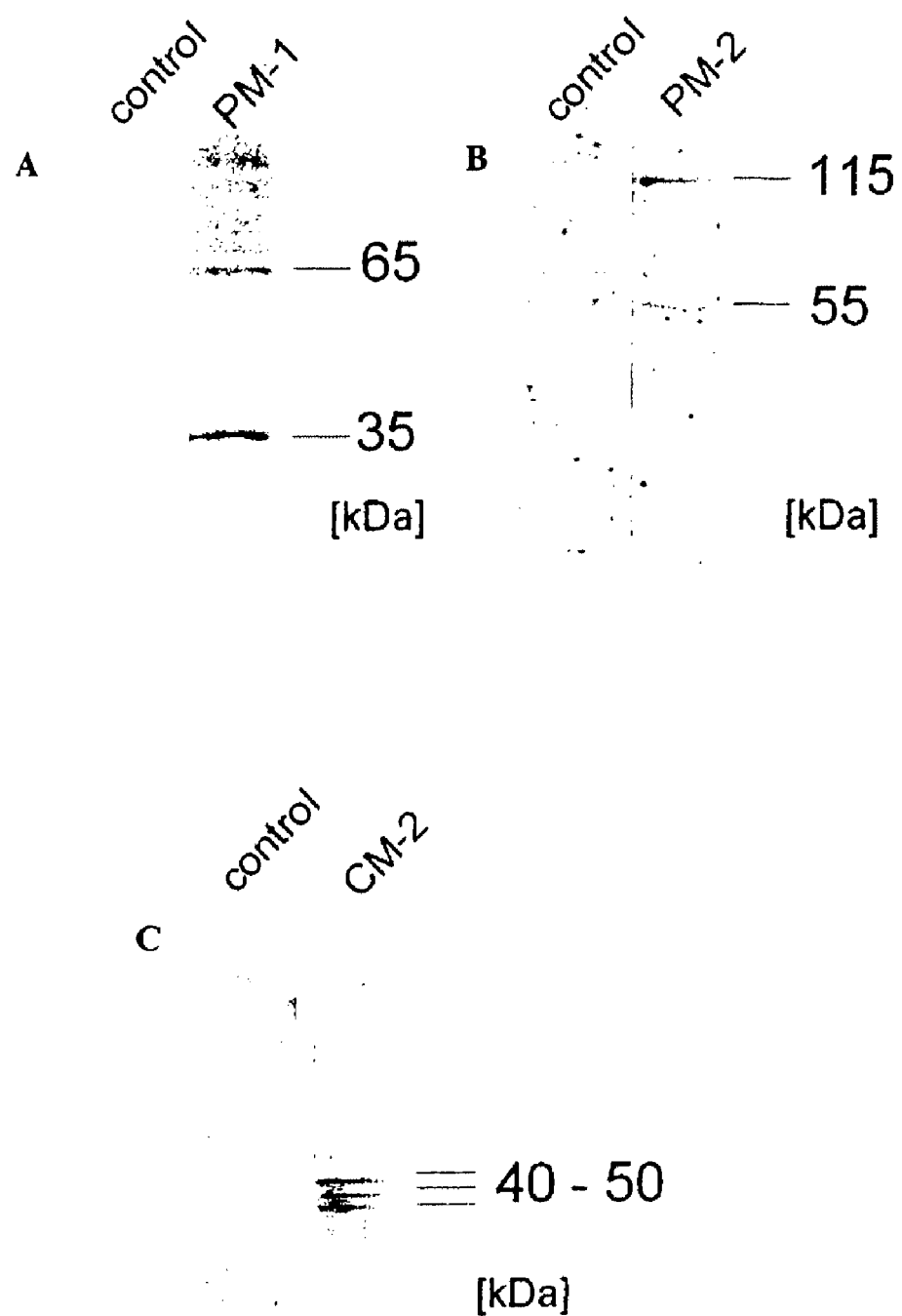
FIGS. 5A-5C is a series of Western blots showing the proteins recognized by human monoclonal antibodies PM-1, PM-2, and CM-2 on membrane extracts of carcinoma cell lines.

To examine the antigens recognized by the antibodies, Western blots were performed with membrane extracts of established carcinoma cell lines. The antibodies PM-1 and PM-2 produced two specific bands each on pancreas adenocarcinoma cell line BXPC-3. Antibody PM-1 reacted with membrane proteins of about 35 and 65 kDa (FIG. 5A), whereas antibody PM-2 reacted with proteins of about 55 and 115 kDa (FIG. 5B). Antibody CM-2 reacted with antigens between 40 and 50 kDa (FIG. 5C). To rule out non-specific binding of IgM antibodies to membrane extracts, unrelated human control IgM was used as control.

Moreover, the PM-1, PM-2, and CM-2 monoclonal antibodies also specifically stain a number of carcinoma cell lines. In particular, the PM-1 antibody binds to the ASPC-1 pancreatic carcinoma cell line (American Type Culture Collection ("ATCC") Accession No. CRL-1682) and the BXPC-3 pancreatic carcinoma cell line (ATCC Accession No. CRL-1687). The PM-2 antibody specifically binds to the CACO-2 human colorectal adenocarcinoma cell line (ATCC Accession No. HBT-37, DSMZ Accession No. ACC 169), the human colon carcinoma cell line COLO-320 (DSMZ Accession No. ACC 144), the human colon carcinoma cell line COLO-206F (DSMZ Accession No. ACC 21), the HT-29 human colorectal adenocarcinoma cell line (ATCC Accession No. HTB-38), ASPC-1 pancreatic carcinoma cells, and BXPC-3 pancreatic carcinoma cell line. Further, the CM-2 antibody specifically binds to CACO-2 and COLO 206F cells. Slides of these cells were stained according to the cytospin protocol described in the materials and methods section.

EXAMPLE 4

Determining Whether an Antibody Induces Apoptosis

A number of assays standard in the art may be used to determine if an antibody induces apoptosis of a cell.

For example, we used the CELL DEATH DETECTION ELISA$^{PLUS}$ (Roche, Mannheim, Germany) to analyze the extent to which the PM-1, PM-2, and CM-2 antibodies induce apoptosis. The cell death detection ELISA is based on a quantitative sandwich-enzyme-immunoassay principle using mouse monoclonal antibodies directed against DNA and histones, respectively. This assay allows the specific determination of mono- and oligo-nucleosomes which are released into the cytoplasm of cells which die from apoptosis.

Figure 4:
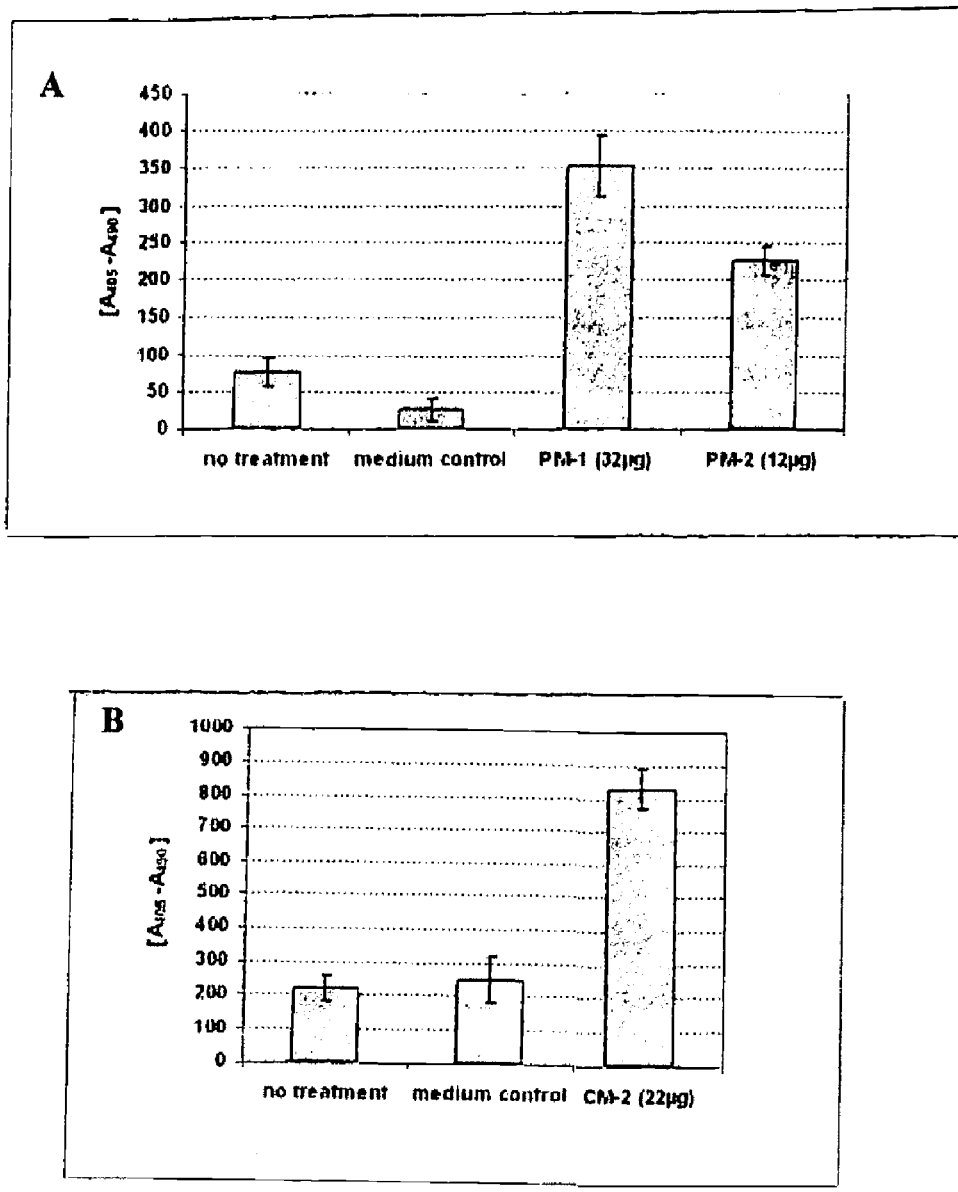
FIGS. 4A and 4B are a series of graphs showing that the PM-1, PM-2, and CM-2 antibodies induce apoptosis. In these experiments, apoptosis was detected using the Cell Death Detection ELISA$^{PLUS}$ apoptosis assay.

In particular, 1×10$^4$ tumor cells (BXPC-3 for PM-1 and PM-2, CACO-2 for CM-2) were plated on 96-well plates and incubated in presence of different concentrations of the human IgM-antibodies for 24 hours at 37° C. and 7% $CO_2$ in an $CO_2$ incubator. Depleted cell culture supernatant with unrelated IgM antibodies served as negative control. After the incubation period, the cells were centrifuged for 10 minutes and the supernatants were removed. The resulting cell pellets were then incubated with lysis-buffer for 30 minutes at room temperature. After centrifugation the supernatants were transferred into a streptavidin-coated microtiter plate (MTP) and immunoreagent (a mixture of 10% Anti-Histone-Biotin, 10% Anti-DNA-peroxidase (Anti-DNA POD) and 80% incubation buffer) added before incubation for 2 hours at room temperature on a MTP shaker at 250 rpm. Following the incubation period, unbound components were removed by a washing step with incubation buffer. POD was determined photometrically with ABTS™ as a substrate (1 ABTS™ (2,2'-Azino-di[3-ethyl-benz-thiazolin-sulfonat) tablet in 5 ml substrate buffer). Antibody-induced apoptosis was measured by determining the color intensity of the green precipitate that it formed as a result of this reaction using an ELISA reader at a wavelength of 415 nm in comparison to ABTS™ solution as a blank (reference wavelength of approximately 490 mm). Based on this color intensity, we calculated the level of the antibody-induced apoptosis. These experiments clearly showed that each antibody, PM-1, PM-2, and CM-2, induces apoptosis in carcinoma cells after 24 hours of incubation (FIGS. 4A and 4B).

Figure 7:
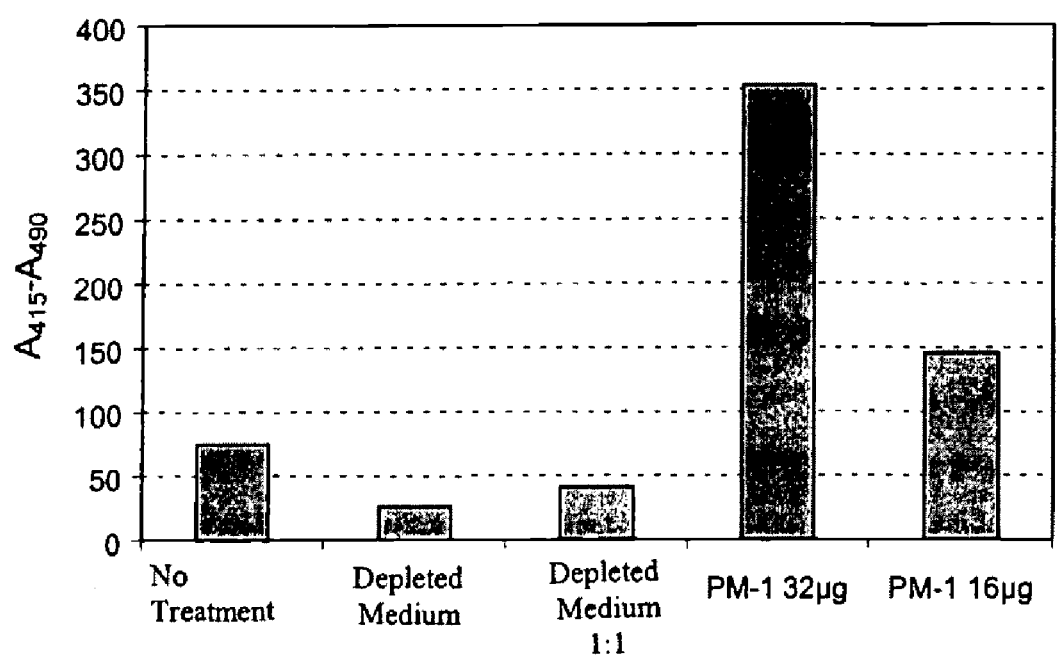
FIG. 7 is a graph of the results of a cell death enzyme-linked immunosorbent assay (ELISA) showing that the PM-1 monoclonal antibody induces apoptosis of BXPC-3 cells after 24 hours of incubation.
Figure 9:
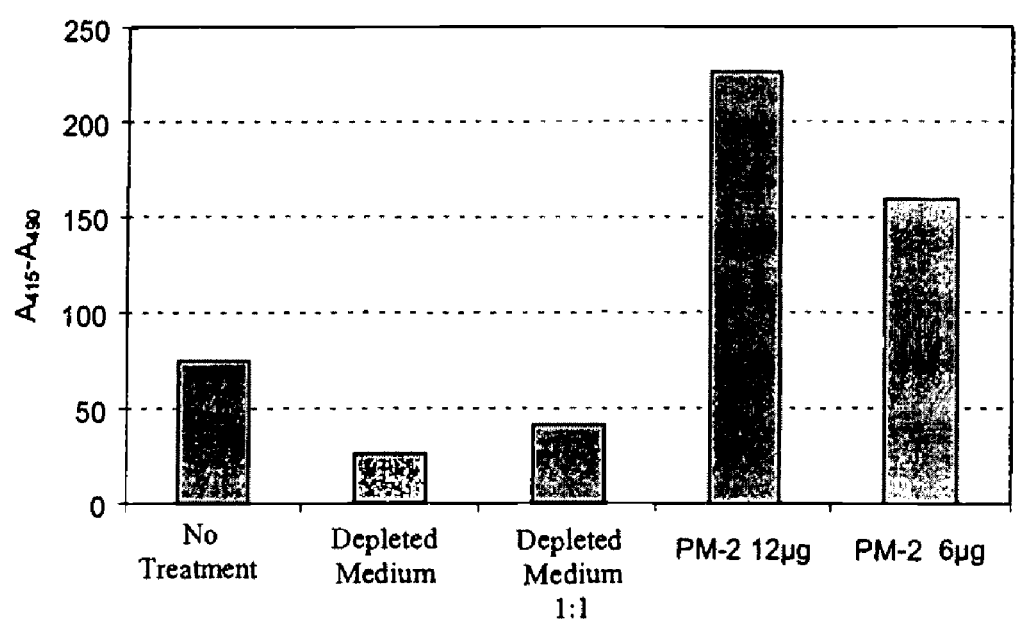
FIG. 9 is a graph of the results of an ELISA showing that the PM-2 monoclonal antibody induces apoptosis of BXPC-3 cells after 24 hours of incubation.

In addition, as is shown in FIGS. 7 and 9, the PM-1 and PM-2 monoclonal antibodies, respectively, induce apoptosis in BXCP-3 human pancreatic carcinoma cells after a 24 hour incubation period when compared to a negative control. The Y-axis in these figures is the difference between the absorbance at 415 nm and at the 490 nm reference wavelength ($A_{415}$-$A_{490}$) and the negative control is RPMI 1460 medium. The concentration of the PM-1 antibody was either 16 μg or 32 μg/ml in supernatant and the concentration of the PM-2 antibody was either 6 μg or 12 μg/ml in supernatant.

Figure 11:
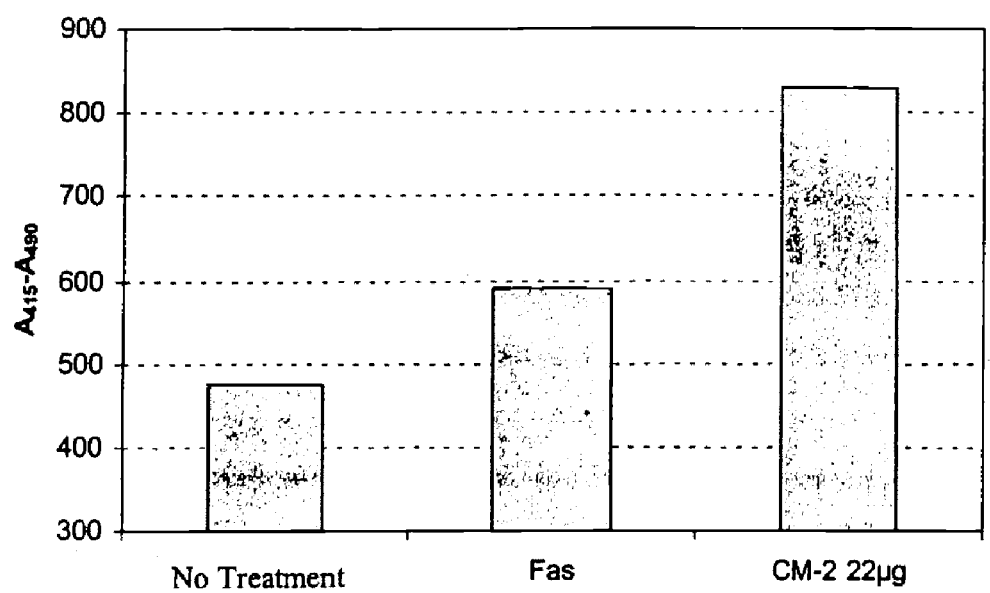
FIG. 11 is a graph of the results of an ELISA showing that the CM-2 monoclonal antibody induces apoptosis of CACO-2 cells after 24 hours of incubation.

As is shown in FIG. 11, CM-2 induces apoptosis of CACO-2 human colorectal carcinoma cells after a 24 hour incubation. Again, the Y-axis in this figure is the difference between the absorbance at 415 nm and at the 490 nm reference wavelength ($A_{415}$-$A_{490}$). The negative control is RPMI 1460 medium. As is shown in FIG. 11, both a commercially available CD95 Fas antibody at 2 μg/ml and the supernatant containing the CM-2 monoclonal antibody (22 μg/ml) induce apoptosis when compared to the negative control.

EXAMPLE 5

Determining Whether an Antibody Inhibits Cell Proliferation

Cell proliferation may be assayed by a number of methods that are standard in the art, for example, by the reduction of tetrazolium salts. The yellow tetrazolium salt 3-(4,5-dimethylthiazol-2-yl)-2,5-diphenyltetrazolium bromide ("MTT") (Sigma, St. Louis, Mo.), is reduced by metabolically active cells, in part by the action of mitochondrial dehydrogenase enzymes to generate reducing equivalents such as NADH and NADPH. The resulting intracellular purple formazan can be solubilized and quantified by spectrophotometric means. The MTT cell proliferation assay measures the rate of cell proliferation and, when metabolic events lead to apoptosis, the reduction in cell viability.

For the MTT assay, we trypsinized cells (BXPC-3 for PM-1 and PM-2, Colo-206F for CM-2) and resuspended the cells in 10 ml of RPMI-1460 medium contains 10% Fetal Calf Serum (FCS), 1% glutamine, and 1% penicillin/streptomycin (complete medium). The cells were then counted and diluted to 1×10$^6$ cells/ml. 50 μl of this suspension were pipetted into wells of a 96-well plate, resulting in approximately 5×10$^4$ cells/well. The first row of wells was left empty. We then added 50 μl of the antibody diluted in complete medium to each well. The 96-well plate was then incubated for 24 or 48 hours in a 37° C. incubator. After the incubation period, 50 μl MTT solution (5 mg/ml in PBS) were added to each well. The 96-well plate was incubated for 30 minutes at 37° C. and centrifuged for 5 minutes at 800×g. The supernatant was aspirated, 150 μl of dimethylsulphoxide (DMSO) were added to each well, and the cell pellet was resuspended. Absorption was determined at a wavelength of 540 nm and at a reference wavelength of 690 nm in an ELISA reader.

Figure 3:
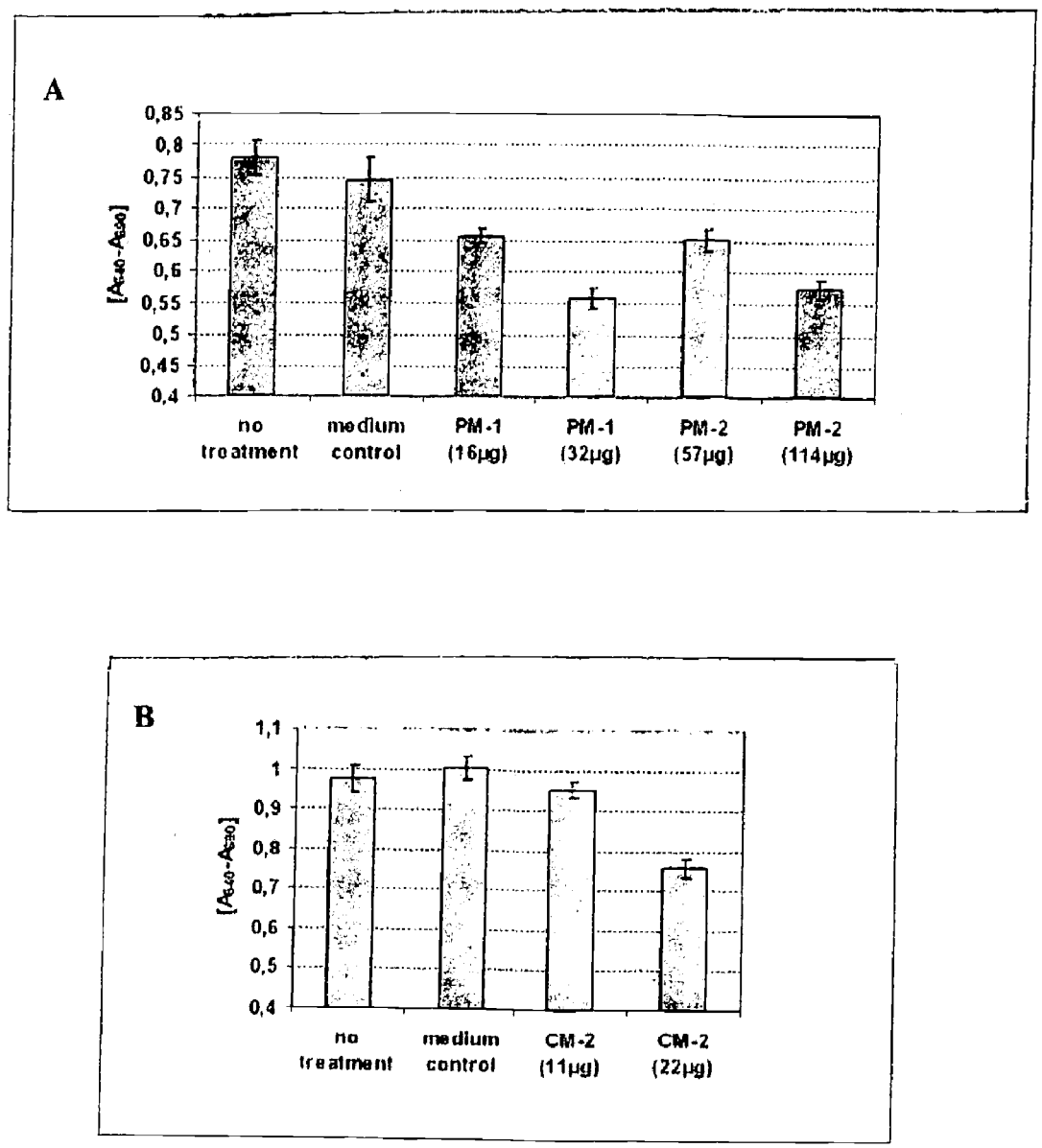
FIGS. 3A and 3B are a series of graphs depicting the functional analysis of antibodies PM-1, PM-2, and CM-2 in vitro. The consequences of antibody treatment on the proliferation of different carcinoma cell lines were measured using an MTT proliferation assay.

After 24 or 48 hours, the PM-1, PM-2, and CM-2 antibodies inhibited cell proliferation of the respective tumor cell lines in a concentration-dependent manner, while the controls with depleted cell culture supernatant remained unchanged (FIGS. 3A and 3B).

Figure 6:
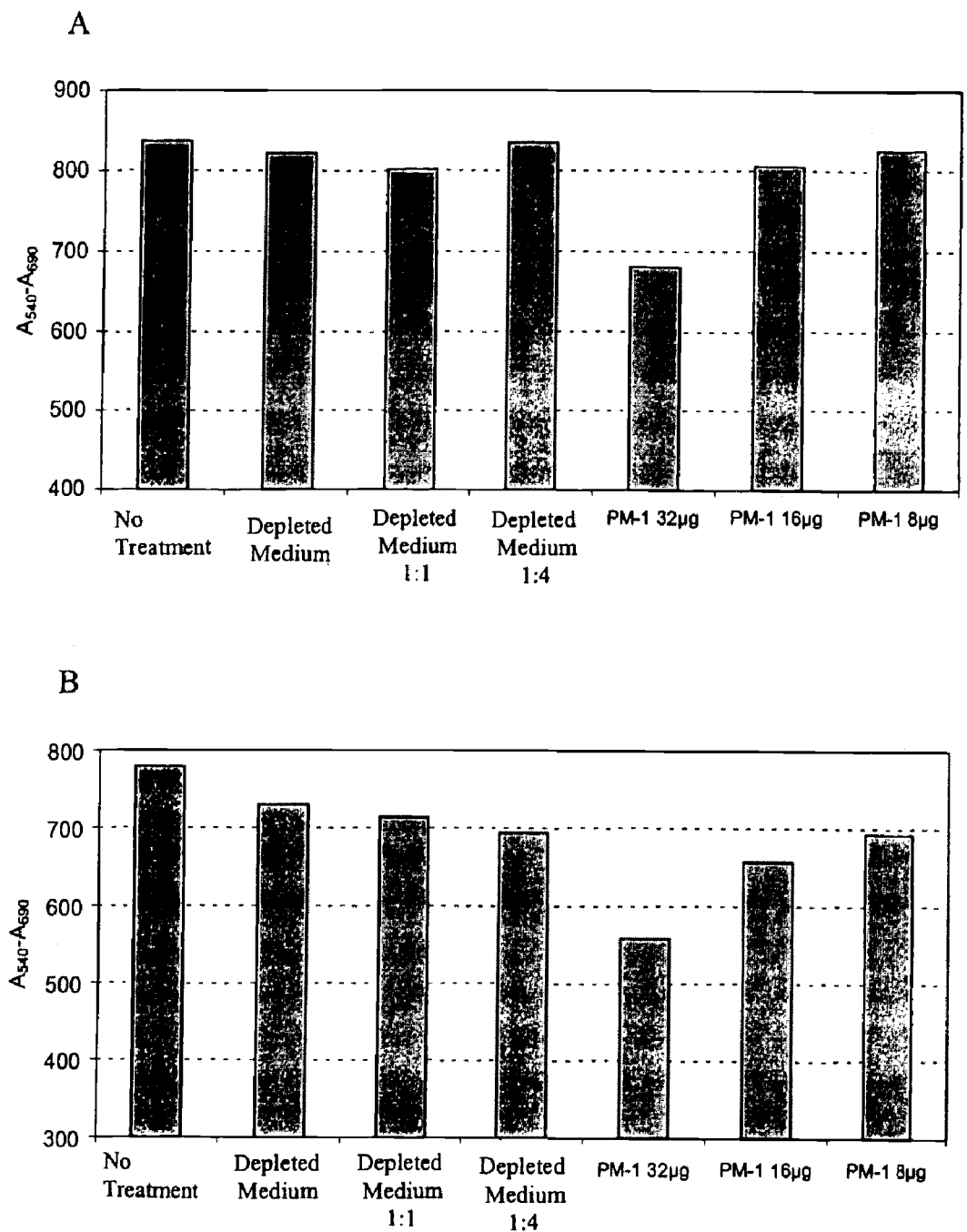
FIGS. 6A and 6B are a series of graphs of the results of 3-(4,5-dimethylthiazol-2-yl)-2,5-diphenyltetrazolium bromide (MTT) reduction assays for mitochondrial dehydrogenase activity showing that the PM-1 monoclonal antibody inhibits cell proliferation and decreases survival, or induces apoptosis of BXPC-3 pancreatic carcinoma cells after 24 hours of incubation (FIG. 6A) and after 48 hours of incubation (FIG. 6B).
Figure 8:
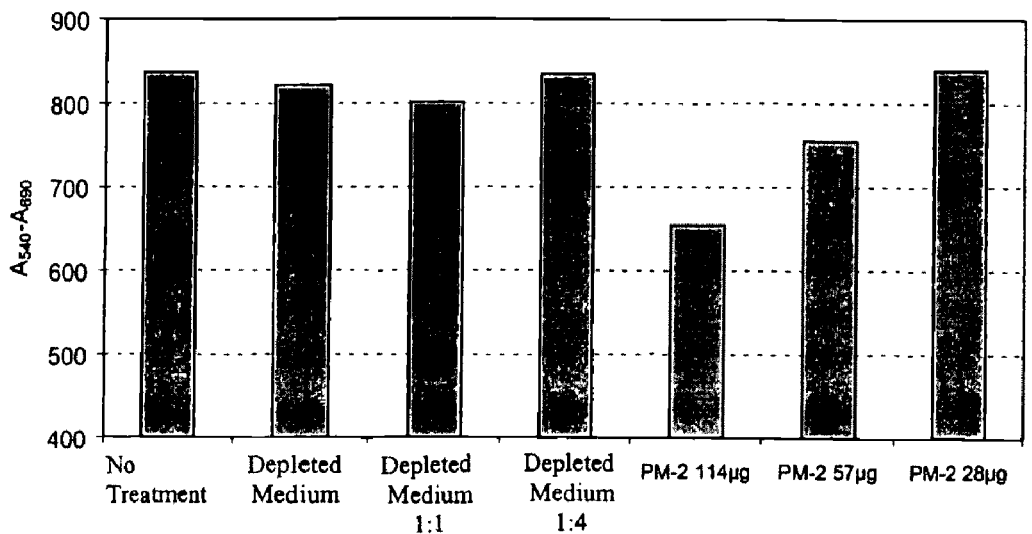
FIGS. 8A and 8B are a series of graphs of the MTT reduction assays for mitochondrial dehydrogenase activity showing that the PM-2 monoclonal antibody inhibits cell proliferation and decreases survival, or induces apoptosis of BXPC-3 pancreatic carcinoma cells after 24 hours of incubation (FIG. 8A) and after 48 hours of incubation (FIG. 8B).
Figure 8:
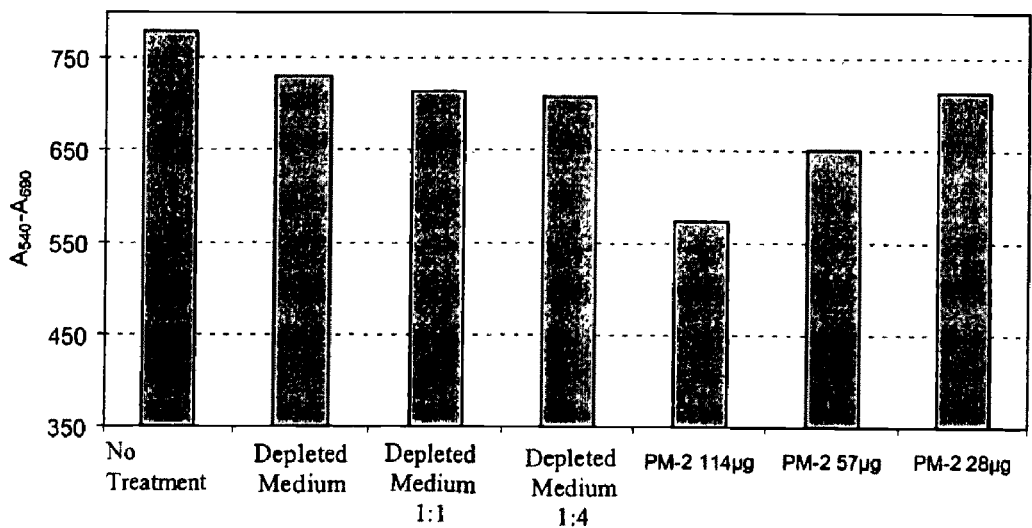
Figure 10:
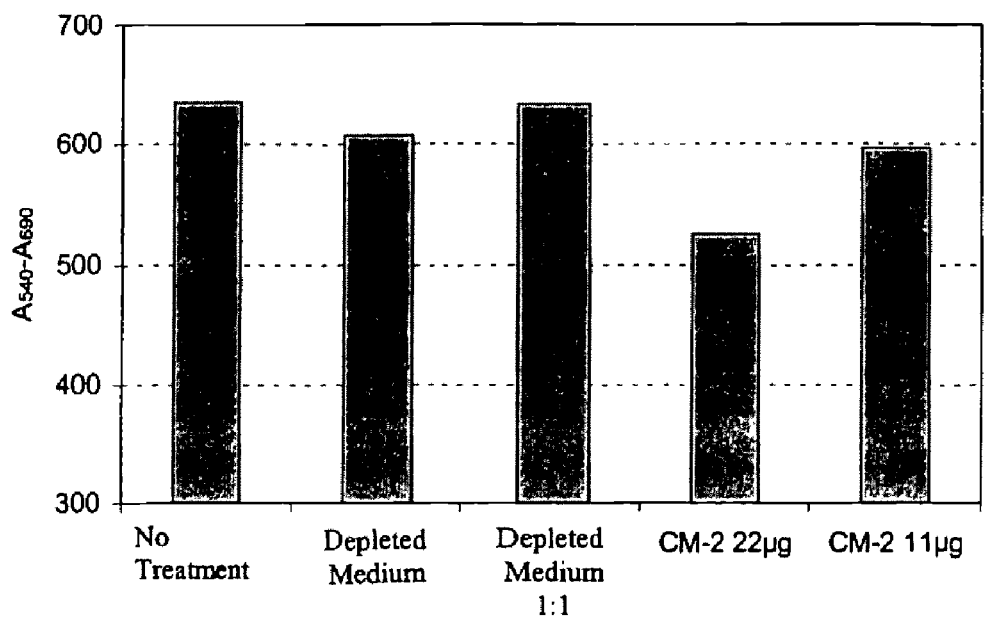
FIGS. 10A and 10B are a series of graphs of the results of MTT reduction assays for mitochondrial dehydrogenase activity showing that the CM-2 monoclonal antibody inhibits cell proliferation and decreases survival, or induces apoptosis of COLO-206F colon carcinoma cells after 24 hours of incubation (FIG. 10A) and after 48 hours of incubation (FIG. 10B).
Figure 10:
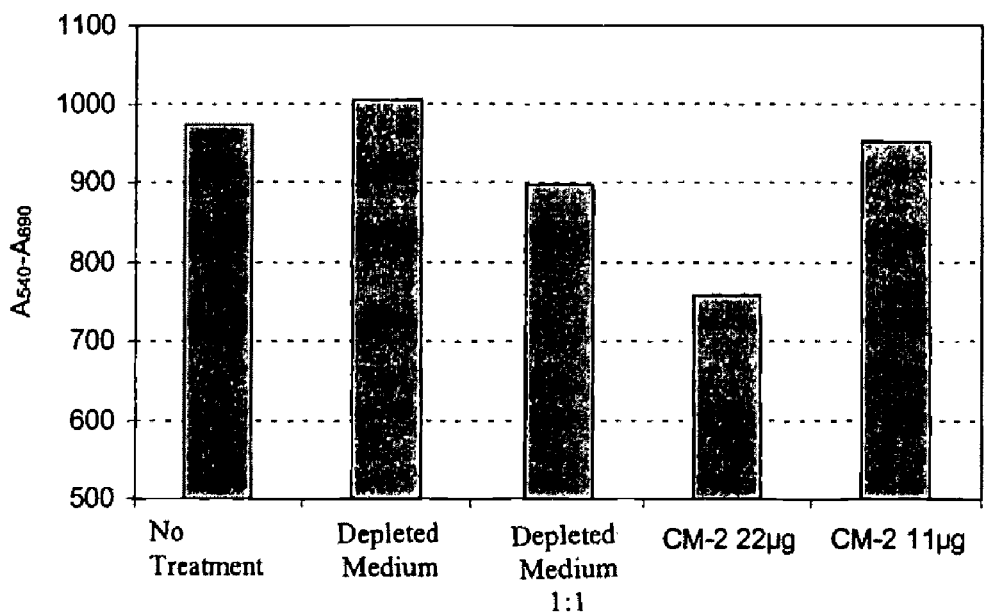

Further exemplary results of such experiments are depicted in FIGS. 6A, 6B, 8A, 8B, 10A, and 10B. FIGS. 6A and 6B show the results of experiments using BXPC-3 pancreatic carcinoma cells that were incubated with the PM-1 monoclonal antibody, with depleted supernatant, or without an antibody for 24 hours (FIG. 6A) or 48 hours (FIG. 6B). The y-axis shows the difference in absorbance at 540 nm and 690 nm ($A_{540}$-$A_{690}$). As is evident from these graphs, incubation with the PM-1 monoclonal antibody resulted in a decrease in cell proliferation and cell viability after both a 24 hour and a 48 hour incubation period. Similarly, as is shown in FIGS. 8A and 8B, incubation of BXPC-3 cells with the PM-2 monoclonal antibody resulted in a decrease in proliferation and cell viability after both a 24 hour (FIG. 8A) and a 48 hour period (FIG. 8B). In addition, as is shown in FIGS. 10A and 10B, incubation of COLO-206F colon carcinoma cells with the CM-2 monoclonal antibody resulted in a decrease in proliferation and cell viability after both a 24 hour (FIG. 10A) and a 48 hour period (FIG. 10B).

EXAMPLE 6

In Vivo Imaging of a Neoplasm

A patient suspected of having a neoplasm, such as a colorectal carcinoma, may be given a dose of radioiodinated PM-1, PM-2, or CM-2 antibody, or another tumor-specific polypeptide, and radiolabeled unspecific antibody using the methods described herein. Localization of the tumor for imaging may be effected according to the procedure of Goldenberg et al. (N. Engl. J. Med., 298:1384, 1978). By I.V. an infusion of equal volumes of solutions of $^{131}$I-PM-1, PM-2, or CM-2 antibody and Tc-99m-labeled unspecific antibody may be administered to a patient. Prior to administration of the reagents I.V., the patient is typically pre-tested for hypersensitivity to the antibody preparation (unlabeled) or to antibody of the same species as the antibody preparation. To block thyroid uptake of $^{131}$I, Lugol's solution is administered orally, beginning one or more days before injection of the radioiodinated antibody, at a dose of 5 drops twice or three-times daily. Images of various body regions and views may be taken at 4, 8, and 24 hours after injection of the labeled preparations. If present, the neoplasm, e.g., a colorectal carcinoma, is detected by gamma camera imaging with subtraction of the Tc-99m counts from those of $^{131}$I, as described for $^{131}$I-labeled anti-CEA antibody and Tc-99m-labeled human serum albumin by DeLand et al. (Cancer Res. 40:3046, 1980). At 8 hours after injection, imaging is usually clear and improves with time up to the 24 hour scans.

EXAMPLE 7

Treatment of a Neoplasm Using Labeled Antibody Mixtures

A patient diagnosed with a neoplasm, for example, a female patient diagnosed with a breast carcinoma, may be treated with the polypeptides of the invention as follows. Lugol's solution may be administered, e.g., 7 drops 3 times daily, to the patient. Subsequently, a therapeutic dose of $^{131}$I-PM-1, PM-2, or CM-2 antibody may be administered to the patient. For example, a $^{131}$I dose of 50 mCi may be given weekly for 3 weeks, and then repeated at intervals adjusted on an individual basis, e.g., every three months, until hematological toxicity interrupts the therapy. The exact treatment regimen is generally determined by the attending physician or person supervising the treatment. The radioiodinated antibodies may be administered as slow I.V. infusions in 50 ml of sterile physiological saline. After the third injection dose, a reduction in the size of the primary tumor and metastases may be noted, particularly after the second therapy cycle, or 10 weeks after onset of therapy.

EXAMPLE 8

Treatment Using Conjugated Antibodies

A patient diagnosed with a neoplasm, for example, a female patient with breast cancer that has metastasized to the chest and lungs, may be treated with solutions of $^{131}$I-PM-1, PM-2, or CM-2, $^{10}$B-PM-1, PM-2, or CM-2, and a Tc-99m labeled unspecific antibody. An amount of $^{131}$I-labeled PM-1, PM-2, or CM-2 antibody (in 50 ml of sterile physiological saline) sufficient to provide 100 mCi of $^{131}$I activity based on a 70 kg patient weight may be administered to the patient. This dosage is equal to 3.3 mg of an antibody having 40-80 Boron atoms and 8-16 Boron-10 atoms per antibody molecule. The neoplasm is first precisely localized using the procedure of Example 6. In addition, Lugol's solution should be continuously administered to the patient, as in the previous example. A well-collimated beam of thermal neutrons may then be focused on the defined tumor locations. Irradiation with an external neutron beam dose of 400-800 rads, delivered in a period of from 8-20 min, is effected for each tumor locus, and is optionally repeated with administration of the tumor-locating antibody, with or without the radiolabel, at intervals adjusted on an individual basis, but usually not exceeding a total dose of 3200 rads unless simultaneous external irradiation therapy is indicated. If desired, in addition to this therapy, an anti-tumor agent, such as a chemotherapeutic agent, may also be administered to the patient.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

German Patent Application Nos. 102 29 907.2, 102 30 516.1, 102 29 906.4, U.S. Pat. Nos. 5,367,060 and 5,641,869, and all other references cited herein are hereby incorporated by reference.

We claim:

1. A purified antibody or antigen binding fragment thereof comprising a light chain ($V_L$) variable region sequence and a heavy chain ($V_H$) variable region sequence, wherein the light chain ($V_L$) variable region sequence comprises amino acids 26-31, 49-51, and 88-95 of SEQ ID NO:1, or wherein the heavy chain ($V_H$) variable region sequence comprises amino acids 11-18, 36-43, and 82-90 of SEQ ID NO:3, and wherein said antibody or antigen binding fragment specifically binds to an epitope of a polypeptide expressed by at least one of ASPC-1 (ATCC Accession No. CRL-1682), or BXPC-3 (ATCC Accession No. CRL-1687) cells, and wherein PM-1 antibody produced by a cell line deposited as DSM ACC 2599 specifically binds to said epitope of the polypeptide expressed by at least one of ASPC-1 (ATCC Accession No. CRL-1682), or BXPC-3 (ATCC Accession No. CRL-1687) cells.

2. The purified antibody or antigen binding fragment of claim 1, wherein said antibody or antigen binding fragment binds to a stomach adenocarcinoma, colorectal adenocarcinoma, squamous cell lung carcinoma, lung adenocarcinoma, squamous cell carcinoma of the esophagus, adenocarcinoma of the pancreas, adenocarcinoma of the prostate, ductal carcinoma of the breast, lobular carcinoma of the breast, adenocarcinoma of the ovary, or adenocarcinoma of the uterus cell.

3. The purified antibody or antigen binding fragment of claim 1, wherein said antibody or antigen binding fragment binds to BXPC-3 (ATCC Accession No. CRL-1687) cells.

4. The purified antibody or antigen binding fragment of claim 1, wherein said antibody or antigen binding fragment binds to ASPC-1 (ATCC Accession No. CRL-1682) cells.

5. The purified antibody or antigen binding fragment of claim 1, wherein said antigen binding fragment is selected from the group consisting of $F_v$, Fab, Fab', and $F(ab')_2$.

6. The purified antibody or antigen binding fragment of claim 1, wherein said antigen binding fragment comprises the sequence of SEQ ID NO:1 or SEQ ID NO:3.

7. The purified antibody or antigen binding fragment of claim 1, wherein the light chain ($V_L$) variable region sequence comprises the amino acid sequence of SEQ ID NO:1.

8. The purified antibody or antigen binding fragment of claim 1, wherein the light chain ($V_L$) variable region sequence comprises amino acid 26-31, 49-51, and 88-95 of SEQ ID NO:1.

9. The purified antibody or antigen binding fragment of claim 1, wherein the heavy chain ($V_H$) variable region sequence comprises the amino acid sequence of SEQ ID NO:3.

10. The purified antibody or antigen binding fragment of claim 1, wherein the heavy chain ($V_H$) variable region sequence comprises amino acids 11-18, 36-43, and 82-90 of SEQ ID NO:3.

11. A purified antibody or antigen binding fragment comprising the amino acid sequence of SEQ ID NOS:1 and 3.

12. A purified antibody or antigen binding fragment comprising a light chain ($V_L$) variable region sequence and a heavy chain ($V_H$) variable region sequence, wherein the light chain ($V_L$) variable region comprises amino acid 26-31, 49-51, and 88-95 of SEQ ID NO:1 and wherein the heavy chain ($V_H$) variable region comprises amino acids 11-18, 36-43, and 82-90 of SEQ ID NO:3.

13. The purified antibody or antigen binding fragment of claims 1, 11 or 12, wherein said antibody or antigen binding fragment is a monoclonal antibody.

14. The purified antibody or antigen binding fragment of claim 13, wherein said monoclonal antibody is a human monoclonal antibody.

15. A purified antibody produced by the PM-1 cell line having DSMZ Accession No. DSM ACC2599.

16. A purified or isolated cell that expresses the antibody or antigen binding fragment of claims 1, 11 or 12.

17. The cell of claim 16, wherein said cell is a hybridoma.

18. The purified antibody or antigen binding fragment of claim 1, wherein said antibody or antigen binding fragment induces apoptosis of ASPC-1 (ATCC Accession No. CRL-1682), or BXPC-3 (ATCC Accession No. CRL-1687) cells.

19. The purified antibody or antigen binding fragment of claim 12, wherein said antibody or antigen binding fragment induces apoptosis of ASPC-1 (ATCC Accession No. CRL-1682), or BXPC-3 (ATCC Accession No. CRL-1687) cells.

* * * * *